(12) United States Patent
Poole et al.

(10) Patent No.: US 9,725,755 B2
(45) Date of Patent: Aug. 8, 2017

(54) SYNTHESIS AND ENRICHMENT OF NUCLEIC ACID SEQUENCES

(71) Applicant: Trovagene, Inc., San Diego, CA (US)

(72) Inventors: Jason Poole, San Diego, CA (US); Saege Handcock, San Diego, CA (US); Karena Kosco, San Diego, CA (US); Vlada Melnikova, San Diego, CA (US); Peter Croucher, San Diego, CA (US); Tim Lu, San Diego, CA (US); Mark Erlander, San Diego, CA (US); Errin Samuelsz, San Diego, CA (US)

(73) Assignee: Trovagene, Inc., San Diego, CA (US)

(*) Notice: Subject to any disclaimer, the term of this patent is extended or adjusted under 35 U.S.C. 154(b) by 0 days.

(21) Appl. No.: 15/256,523

(22) Filed: Sep. 3, 2016

(65) Prior Publication Data

US 2017/0009276 A1 Jan. 12, 2017

Related U.S. Application Data

(63) Continuation of application No. 15/027,688, filed as application No. PCT/US2014/061435 on Oct. 20, 2014.

(60) Provisional application No. 61/893,283, filed on Oct. 20, 2013, provisional application No. 61/904,141, filed on Nov. 14, 2013, provisional application No. 62/039,905, filed on Aug. 20, 2014.

(51) Int. Cl.
*C12Q 1/68* (2006.01)
*C12P 19/34* (2006.01)

(52) U.S. Cl.
CPC .......... *C12Q 1/6806* (2013.01); *C12Q 1/686* (2013.01); *C12Q 1/6827* (2013.01); *C12Q 1/6886* (2013.01); *C12Q 2600/156* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 5,849,497 A | * 12/1998 | Steinman | C12Q 1/686 435/6.11 |
| 8,206,929 B2 | 6/2012 | Grow et al. | |
| 8,455,190 B2 | 6/2013 | Makrigiorgos | |
| 8,623,603 B2 | 1/2014 | Makrigiorgos | |

(Continued)

FOREIGN PATENT DOCUMENTS

| | | |
|---|---|---|
| WO | 03072809 A1 | 9/2003 |
| WO | 2012075231 A1 | 6/2012 |
| WO | 2012162613 A2 | 11/2012 |

OTHER PUBLICATIONS

Vikis et al., "EGFR-T790M Is a Rare Lung Cancer Susceptibility Allele with Enhanced Kinase Activity," Cancer Research, 2007, vol. 67, No. 10, pp. 4665-4670.*

(Continued)

*Primary Examiner* — Young J Kim
(74) *Attorney, Agent, or Firm* — Lewis Roca Rothgerber Christie LLP; Holly P. Logue; Elie H. Gendloff

(57) ABSTRACT

The present disclosure relates to the enrichment of target nucleic acid sequences present in low-abundance relative to corresponding non-target or reference nucleic acid sequence in a sample. In particular, the methods allow for a substantially greater level of detection sensitivity of target sequence by orders of magnitude enrichment of a low-abundance sequence.

20 Claims, 13 Drawing Sheets

(56) References Cited

U.S. PATENT DOCUMENTS

| | | | |
|---|---|---|---|
| 9,005,932 B2 | 4/2015 | Cobb | |
| 9,133,490 B2 | 9/2015 | Candau-Chacon | |
| 2007/0264653 A1* | 11/2007 | Berlin | C12Q 1/6816 435/6.16 |
| 2010/0068711 A1 | 3/2010 | Umansky et al. | |
| 2011/0217714 A1 | 9/2011 | Makrigiorgos | |
| 2013/0149695 A1 | 6/2013 | Lee et al. | |
| 2013/0178383 A1* | 7/2013 | Spetzler | G01N 33/5432 506/9 |

OTHER PUBLICATIONS

BinLaden et al., "The Use of Coded PCR Primers Enables High-Throughput Sequencing of Mulitple Homolog Amplification Products by 454 Parallel Sequencing," PLos One, 2007, issue 2, e197, pp. 1-9.*

Dominguez et al., "Wild-type blocking polymerase chain reaction for detection of single nucleotide minority mutations from clinical specimens," Oncogene, 2005, vol. 24, pp. 6830-6834.*

Lee et al., "Mutant Enrichment with 3'-Modified Oligonucleotides," The Journal of Molecular Diagnostics, Nov. 2011, vol. 13, No. 6, pp. 657-668.*

Li et al., Replacing PCR with COLD-PCR enriches variant DNA sequences and redefines the sensitivity of genetic testing, Nature Medicine, 2008, 579-584, 14-5.

Liew et al., Genotyping of Single-Nucleotide Polymorphisms by High-Resolution Melting of Small Amplicons, Clinical Chemistry, 2004, 1156-1164, 50-7.

Lipsky et al., DNA Melting Analysis for Detection of Single Nucleotide Polymorphisms, Clinical Chemistry, 2001, 635-644, 47-4.

Luthra et al., COLD-PCR Finds Hot Application in Mutation Analysis, Clinical Chemistry, 2009, 2077-2078, 55-12.

Wang et al., Allele-Specific, Non-Extendable Primer Blocker PCR (AS-NEPB-PCR) for DNA Mutation Detection in Cancer, Journal of Molecular Diagnostics, 2013, 62-69, vol. 15, Elsevier.

Morlan et al., Mutation Detection by Real-Time PCR: A Simple, Robust and Highly Selective Method, PLoS ONE, 2009, e4584, vol. 4 Issue 2.

* cited by examiner

| EXPECTED/ OBSERVED | 0 | 1 | 2 | 3 | 4 | 5 | 7 |
|---|---|---|---|---|---|---|---|
| 0 | 100% | 0% | 0% | 0% | 0% | 0% | 0% |
| 0.13 | 88% | 11% | 1% | 0% | 0% | 0% | 0% |
| 0.25 | 78% | 19% | 2% | 0% | 0% | 0% | 0% |
| 0.5 | 61% | 30% | 8% | 1% | 0% | 0% | 0% |
| 1 | 37% | 37% | 18% | 6% | 2% | 0% | 0% |
| 2 | 14% | 27% | 27% | 18% | 9% | 4% | 1% |
| 3 | 5% | 15% | 22% | 22% | 17% | 10% | 5% |

SEQUENCE LISTING

<160> NUMBER OF SEQ ID NOS: 86

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
acactgacga catggttcta ca                                              22

<210> SEQ ID NO 2
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
actgtccagc tttgtgcc                                                   18

<210> SEQ ID NO 3
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
acactgacga catggttcta caactgtcca gctttgtgcc                           40

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gatcatcata ggagttgcat tgttg                                           25

<210> SEQ ID NO 5
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
acactgacga catggttcta cagatcatca taggagttgc attgttg                   47

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tacggtagca gagacttggt ct                                              22

```
<210> SEQ ID NO 7
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tcctctgcct aggcgtt                                                    17

<210> SEQ ID NO 8
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tacggtagca gagacttggt cttcctctgc ctaggcgtt                            39

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gaaatgtaaa tgtggagcca aaca                                            24

<210> SEQ ID NO 10
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tacggtagca gagacttggt ctgaaatgta aatgtggagc caaaca                    46

<210> SEQ ID NO 11
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: C3 spacer modified nucleotide
<220> FEATURE:
<221> NAME/KEY: modified_base
<222> LOCATION: (14)..(14)
<223> OTHER INFORMATION: C3 spacer modified nucleotide

<400> SEQUENCE: 11
cggcctcttc atgc                                                       14

<210> SEQ ID NO 12
<211> LENGTH: 14
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: C3 spacer modified nucleotide
<220> FEATURE:
<221> NAME/KEY: modified_base
<222> LOCATION: (14)..(14)
<223> OTHER INFORMATION: PO4 modified nucleotide

<400> SEQUENCE: 12
cggcctcttc atgc                                                     14

<210> SEQ ID NO 13
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: C3 spacer modified nucleotide
<220> FEATURE:
<221> NAME/KEY: modified_base
<222> LOCATION: (15)..(15)
<223> OTHER INFORMATION: C3 spacer modified nucleotide

<400> SEQUENCE: 13
gattttgggc tggcc                                                    15

<210> SEQ ID NO 14
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: C3 spacer modified nucleotide
<220> FEATURE:
<221> NAME/KEY: modified_base
<222> LOCATION: (14)..(14)
<223> OTHER INFORMATION: C3 spacer modified nucleotide

<400> SEQUENCE: 14
ttttgggctg gcca                                                     14

<210> SEQ ID NO 15
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: C3 spacer modified nucleotide
<220> FEATURE:
<221> NAME/KEY: modified_base
<222> LOCATION: (14)..(14)
<223> OTHER INFORMATION: C3 spacer modified nucleotide

<400> SEQUENCE: 15
gcagctcatc acgc                                                     14
```

```
<210> SEQ ID NO 16
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: C3 spacer modified nucleotide
<220> FEATURE:
<221> NAME/KEY: modified_base
<222> LOCATION: (15)..(15)
<223> OTHER INFORMATION: C3 spacer modified nucleotide

<400> SEQUENCE: 16
aatcactgag cagga                                                      15

<210> SEQ ID NO 17
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: C3 spacer modified nucleotide
<220> FEATURE:
<221> NAME/KEY: modified_base
<222> LOCATION: (14)..(14)
<223> OTHER INFORMATION: C3 spacer modified nucleotide

<400> SEQUENCE: 17
ccagccacca tgat                                                       14

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: C3 spacer modified nucleotide
<220> FEATURE:
<221> NAME/KEY: modified_base
<222> LOCATION: (17)..(17)
<223> OTHER INFORMATION: C3 spacer modified nucleotide

<400> SEQUENCE: 18
gattttgggc tggccaa                                                    17

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
acactgacga catggttcta ca                                              22

<210> SEQ ID NO 20
<211> LENGTH: 22
```

-continued

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20
tacggtagca gagacttggt ct                                                  22

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
tgtagaacca tgtcgtcagt gt                                                  22

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 22
agaccaagtc tctgctaccg ta                                                  22

<210> SEQ ID NO 23
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: C3 spacer modified nucleotide
<220> FEATURE:
<221> NAME/KEY: modified_base
<222> LOCATION: (13)..(13)
<223> OTHER INFORMATION: C3 spacer modified nucleotide

<400> SEQUENCE: 23
aggttaaagg tct                                                            13

<210> SEQ ID NO 24
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: C3 spacer modified nucleotide
<220> FEATURE:
<221> NAME/KEY: modified_base
<222> LOCATION: (16)..(16)
<223> OTHER INFORMATION: C3 spacer modified nucleotide

<400> SEQUENCE: 24
acaaagacct ttaacc                                                         16
```

```
<210> SEQ ID NO 25
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: C3 spacer modified nucleotide
<220> FEATURE:
<221> NAME/KEY: modified_base
<222> LOCATION: (18)..(18)
<223> OTHER INFORMATION: C3 spacer modified nucleotide

<400> SEQUENCE: 25
gtacaaagac ctttaacc                                                 18

<210> SEQ ID NO 26
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: C3 spacer modified nucleotide
<220> FEATURE:
<221> NAME/KEY: modified_base
<222> LOCATION: (17)..(17)
<223> OTHER INFORMATION: C3 spacer modified nucleotide

<400> SEQUENCE: 26
gtacaaagac ctttaac                                                  17

<210> SEQ ID NO 27
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: ZNA4 modified nucleotide
<220> FEATURE:
<221> NAME/KEY: modified_base
<222> LOCATION: (2)..(2)
<223> OTHER INFORMATION: pdC
<220> FEATURE:
<221> NAME/KEY: modified_base
<222> LOCATION: (8)..(9)
<223> OTHER INFORMATION: pdC
<220> FEATURE:
<221> NAME/KEY: modified_base
<222> LOCATION: (15)..(15)
<223> OTHER INFORMATION: pdC
<220> FEATURE:
<221> NAME/KEY: modified_base
<222> LOCATION: (16)..(16)
<223> OTHER INFORMATION: pdC-PO4

<400> SEQUENCE: 27
acaaagacct ttaacc                                                   16

<210> SEQ ID NO 28
<211> LENGTH: 13
<212> TYPE: DNA
<213> ORGANISM: Artificial Sequence
```

```
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: C3 spacer modified nucleotide
<220> FEATURE:
<221> NAME/KEY: modified_base
<222> LOCATION: (13)..(13)
<223> OTHER INFORMATION: C3 spacer modified nucleotide

<400> SEQUENCE: 28
catcacgcag ctc                                                            13

<210> SEQ ID NO 29
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
catcacgcag ctc                                                            13

<210> SEQ ID NO 30
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
tcatcacgca gct                                                            13

<210> SEQ ID NO 31
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
tcatcacgca gc                                                             12

<210> SEQ ID NO 32
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
agctgcgtga tg                                                             12

<210> SEQ ID NO 33
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
```
ctgcgtgatg ag                                                          12

<210> SEQ ID NO 34
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
ctcatcacgc agct                                                        14

<210> SEQ ID NO 35
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: C3 spacer modified nucleotide
<220> FEATURE:
<221> NAME/KEY: modified_base
<222> LOCATION: (14)..(14)
<223> OTHER INFORMATION: C3 spacer modified nucleotide

<400> SEQUENCE: 35
ctcatcacgc agct                                                        14

<210> SEQ ID NO 36
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
ctcatcacgc agctc                                                       15

<210> SEQ ID NO 37
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: C3 spacer modified nucleotide
<220> FEATURE:
<221> NAME/KEY: modified_base
<222> LOCATION: (15)..(15)
<223> OTHER INFORMATION: C3 spacer modified nucleotide

<400> SEQUENCE: 37
ctcatcacgc agctc                                                       15

<210> SEQ ID NO 38
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 38
gagctgcgtg atgag                                                    15

<210> SEQ ID NO 39
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: C3 spacer modified nucleotide
<220> FEATURE:
<221> NAME/KEY: modified_base
<222> LOCATION: (15)..(15)
<223> OTHER INFORMATION: C3 spacer modified nucleotide

<400> SEQUENCE: 39
gagctgcgtg atgag                                                    15

<210> SEQ ID NO 40
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gagctgcgtg atga                                                     14

<210> SEQ ID NO 41
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: C3 spacer modified nucleotide
<220> FEATURE:
<221> NAME/KEY: modified_base
<222> LOCATION: (14)..(14)
<223> OTHER INFORMATION: C3 spacer modified nucleotide

<400> SEQUENCE: 41
gagctgcgtg atga                                                     14

<210> SEQ ID NO 42
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
gcatgagctg cgtgatg                                                  17

<210> SEQ ID NO 43
<211> LENGTH: 17
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<221> NAME/KEY: modified_base
<222> LOCATION: (1)..(1)
<223> OTHER INFORMATION: C3 spacer modified nucleotide
<220> FEATURE:
<221> NAME/KEY: modified_base
<222> LOCATION: (17)..(17)
<223> OTHER INFORMATION: C3 spacer modified nucleotide

<400> SEQUENCE: 43
gcatgagctg cgtgatg                                                    17

<210> SEQ ID NO 44
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
gctcatcacg cagctc                                                     16

<210> SEQ ID NO 45
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: C3 spacer modified nucleotide
<220> FEATURE:
<221> NAME/KEY: modified_base
<222> LOCATION: (16)..(16)
<223> OTHER INFORMATION: C3 spacer modified nucleotide

<400> SEQUENCE: 45
gctcatcacg cagctc                                                     16

<210> SEQ ID NO 46
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
gtgcagctca tcacgcagct c                                               21

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: C3 spacer modified nucleotide
<220> FEATURE:
<221> NAME/KEY: modified_base
<222> LOCATION: (21)..(21)
<223> OTHER INFORMATION: C3 spacer modified nucleotide

<400> SEQUENCE: 47
gtgcagctca tcacgcagct c                                              21

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ggtctagcta cagtgaaa                                                  18

<210> SEQ ID NO 49
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: C3 spacer modified nucleotide
<220> FEATURE:
<221> NAME/KEY: modified_base
<222> LOCATION: (18)..(18)
<223> OTHER INFORMATION: C3 spacer modified nucleotide

<400> SEQUENCE: 49
ggtctagcta cagtgaaa                                                  18

<210> SEQ ID NO 50
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ccatcgagat ttcactgt                                                  18

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: C3 spacer modified nucleotide
<220> FEATURE:
<221> NAME/KEY: modified_base
<222> LOCATION: (18)..(18)
<223> OTHER INFORMATION: C3 spacer modified nucleotide

<400> SEQUENCE: 51
ccatcgagat ttcactgt                                                  18

<210> SEQ ID NO 52
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
ttttgggctg gcc                                                              13

<210> SEQ ID NO 53
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: C3 spacer modified nucleotide
<220> FEATURE:
<221> NAME/KEY: modified_base
<222> LOCATION: (13)..(13)
<223> OTHER INFORMATION: C3 spacer modified nucleotide

<400> SEQUENCE: 53
ttttgggctg gcc                                                              13

<210> SEQ ID NO 54
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
ttttgggctg gcca                                                             14

<210> SEQ ID NO 55
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55
agtttggcca gcc                                                              13

<210> SEQ ID NO 56
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: C3 spacer modified nucleotide
<220> FEATURE:
<221> NAME/KEY: modified_base
<222> LOCATION: (13)..(13)
<223> OTHER INFORMATION: C3 spacer modified nucleotide

<400> SEQUENCE: 56
agtttggcca gcc                                                              13

<210> SEQ ID NO 57
<211> LENGTH: 16
<212> TYPE: DNA
<213> ORGANISM: Artificial Sequence
<220> FEATURE:

<223> OTHER INFORMATION: Description of Artificial Sequence: Synthetic
      oligonucleotide

<400> SEQUENCE: 57
cagtttggcc agccca                                                          16

<210> SEQ ID NO 58
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: C3 spacer modified nucleotide
<220> FEATURE:
<221> NAME/KEY: modified_base
<222> LOCATION: (16)..(16)
<223> OTHER INFORMATION: C3 spacer modified nucleotide

<400> SEQUENCE: 58
cagtttggcc agccca                                                          16

<210> SEQ ID NO 59
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 59
ctcctcttga cctg                                                            14

<210> SEQ ID NO 60
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (1)..(1)
<223> OTHER INFORMATION: C3 spacer modified nucleotide
<220> FEATURE:
<221> NAME/KEY: modified_base
<222> LOCATION: (14)..(14)
<223> OTHER INFORMATION: C3 spacer modified nucleotide

<400> SEQUENCE: 60
ctcctcttga cctg                                                            14

<210> SEQ ID NO 61
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
acactgacga catggttcta cacacagatt ttgggc                                    36

<210> SEQ ID NO 62
<211> LENGTH: 37
<212> TYPE: DNA

-continued

<213> ORGANISM: Artificial Sequence
<220> FEATURE:
<223> OTHER INFORMATION: Description of Artificial Sequence: Synthetic
      primer

<400> SEQUENCE: 62
acactgacga catggttcta catcacagat tttgggc                              37

<210> SEQ ID NO 63
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
acactgacga catggttcta cagatcacag attttgggc                            39

<210> SEQ ID NO 64
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
acactgacga catggttcta caagatcaca gattttggg                            39

<210> SEQ ID NO 65
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
acactgacga catggttcta caagatcaca gattttgg                             38

<210> SEQ ID NO 66
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
acactgacga catggttcta caagatcaca gattttg                              37

<210> SEQ ID NO 67
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
acactgacga catggttcta cagatcacag attttgg                              37

<210> SEQ ID NO 68
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
acactgacga catggttcta cagtcaagat cacagatttt                          40

<210> SEQ ID NO 69
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
acactgacga catggttcta catcaagatc acagatttt                           39

<210> SEQ ID NO 70
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
tacggtagca gagacttggt ctcgcaccca gcagtt                              36

<210> SEQ ID NO 71
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
tacggtagca gagacttggt ctcgcaccca gcagt                               35

<210> SEQ ID NO 72
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
tacggtagca gagacttggt ctgcacccag cagtt                               35

<210> SEQ ID NO 73
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
tacggtagca gagacttggt ctccgcaccc agcag                               35

<210> SEQ ID NO 74
<211> LENGTH: 35
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 74
tacggtagca gagacttggt ctttccgcac ccagc                                  35

<210> SEQ ID NO 75
<211> LENGTH: 15
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: C3 spacer modified nucleotide
<220> FEATURE:
<221> NAME/KEY: modified_base
<222> LOCATION: (15)..(15)
<223> OTHER INFORMATION: C3 spacer modified nucleotide

<400> SEQUENCE: 75
agtttggcca gccca                                                        15

<210> SEQ ID NO 76
<211> LENGTH: 15
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: C3 spacer modified nucleotide
<220> FEATURE:
<221> NAME/KEY: modified_base
<222> LOCATION: (15)..(15)
<223> OTHER INFORMATION: C3 spacer modified nucleotide

<400> SEQUENCE: 76
cagtttggcc agccc                                                        15

<210> SEQ ID NO 77
<211> LENGTH: 15
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: C3 spacer modified nucleotide
<220> FEATURE:
<221> NAME/KEY: modified_base
<222> LOCATION: (15)..(15)
<223> OTHER INFORMATION: C3 spacer modified nucleotide

<400> SEQUENCE: 77
tttgggctgg ccaaa                                                        15

<210> SEQ ID NO 78
<211> LENGTH: 15
<212> TYPE: DNA
<213> ORGANISM: Artificial Sequence
<220> FEATURE:
<223> OTHER INFORMATION: Description of Artificial Sequence: Synthetic
      primer
<220> FEATURE:
```

```
<221> NAME/KEY: modified_base
<222> LOCATION: (1)..(1)
<223> OTHER INFORMATION: C3 spacer modified nucleotide
<220> FEATURE:
<221> NAME/KEY: modified_base
<222> LOCATION: (15)..(15)
<223> OTHER INFORMATION: C3 spacer modified nucleotide

<400> SEQUENCE: 78
attttgggct ggcca                                                     15

<210> SEQ ID NO 79
<211> LENGTH: 16
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: C3 spacer modified nucleotide
<220> FEATURE:
<221> NAME/KEY: modified_base
<222> LOCATION: (16)..(16)
<223> OTHER INFORMATION: C3 spacer modified nucleotide

<400> SEQUENCE: 79
gattttgggc tggcca                                                    16

<210> SEQ ID NO 80
<211> LENGTH: 61
<212> TYPE: DNA
<213> ORGANISM: Homo sapiens

<400> SEQUENCE: 80
tctgcctcac ctccaccgtg cagctcatca ygcagctcat gcccttcggc tgcctcctgg    60
a                                                                    61

<210> SEQ ID NO 81
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
acactgacga catggttcta caccaccgtg cagctc                              36

<210> SEQ ID NO 82
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
tacggtagca gagacttggt ctagggcatg agctgc                              36

<210> SEQ ID NO 83
<211> LENGTH: 36
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 83
acactgacga catggttcta caacctccac cgtgca                                36

<210> SEQ ID NO 84
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
tacggtagca gagacttggt ctcgaagggc atgagctgc                             39

<210> SEQ ID NO 85
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
acactgacga catggttcta caccaccgtg caactc                                36

<210> SEQ ID NO 86
<211> LENGTH: 14
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (1)..(1)
<223> OTHER INFORMATION: C3 spacer modified nucleotide
<220> FEATURE:
<221> NAME/KEY: modified_base
<222> LOCATION: (14)..(14)
<223> OTHER INFORMATION: C3 spacer modified nucleotide

<400> SEQUENCE: 86
gctcatcacg cagc                                                        14
```

SYNTHESIS AND ENRICHMENT OF NUCLEIC ACID SEQUENCES

CROSS-REFERENCE TO RELATED APPLICATIONS

This application is a continuation of U.S. application Ser. No. 15/027,688, filed Apr. 6, 2016, which is a 371 of International Application PCT/US2014/061435, filed Oct. 20, 2014, which claims the benefit of U.S. Provisional Application No. 61/893,283, filed Oct. 20, 2013, U.S. Provisional Application No. 61/904,141, filed Nov. 14, 2013, and U.S. Provisional Application No. 62/039,905, filed Aug. 20, 2014, all of which are incorporated by reference herein in their entirety.

FIELD OF THE DISCLOSURE

Mutations in BRAF and KRAS are examples of genetic alterations that confer a survival and growth advantage to cancer cells. Such genetic alterations can be used for selection of targeted therapies. But in a subject, the alterations are present with a large excess of non-altered, wild-type sequences.

This disclosure relates to synthesizing and enriching target nucleic acid sequences containing one or more alterations, or mutation; the target sequence present in low abundance relative to highly similar wild-type sequences present in a biological sample. Preferential and specific enrichment of the target nucleic acid sequence provides a substantially sensitive level of detection not previously achieved. The disclosed methods also allow quantitative detection of the target sequence.

BACKGROUND OF THE DISCLOSURE

Many diseases and especially cancers are associated with genetic mutations such as single point mutations, small base pair insertions/deletions and the like. Almost all current methods for detection of these rare alleles rely on polymerase chain reaction (PCR). However, a major limitation of PCR-based methods is their low sensitivity and preferential amplification of normal (wild-type) sequence due to their greater relative abundance within a sample. Often, detection of a mutant allele is not possible until it represents greater than 5-10% of the total alleles present. Thus, the ability to detect genetic mutations in a background of wild-type DNA sequence where the variant sequence is present at a low percentage relative to non-variant (target) sequence is a beneficial and highly desired.

Modified PCR methods allowing selective amplification of mutant genes without requiring post-amplification sequencing assays have been described. Such methods include Restriction endonuclease-mediated selective PCR: a novel assay for the detection of K-ras mutations in clinical samples. Am J Pathol 153:373-379), Detection of tumor mutations in the presence of excess amounts of normal DNA. Nat Biotechnol 20:186-189; "locked nucleic acid") COLD-PCR (co-amplification at lower denaturation temperature PCR) (Li, J., et al., 2008. Replacing PCR with COLD-PCR enriches variant DNA sequences and redefines the sensitivity of genetic testing. Nat Med 14:579-584.), US20130149695 (Method for detecting genetic mutation by using a blocking primer), U.S. Pat. No. 8,623,603 (Full cold-PCR enrichment with reference blocking sequence); U.S. Pat. No. 8,455,190 (Enrichment of a target sequence); WO2003072809 (Melting Temperature Dependent DNA Amplification) and others.

COLD-PCR technique is relatively simple to perform, but has a low amplification factor (3-100×) and a low sensitivity towards minute temperature changes (Li, J., et al., 2008. Replacing PCR with COLD-PCR enriches variant DNA sequences and redefines the sensitivity of genetic testing. Nat Med 14:579-584, Luthra, R., et al., 2009. COLD-PCR finds hot application in mutation analysis. Clin Chem 55:2077-2078). Other methods, such as that described in Molloy et al. (WO2003072809) requires use of lower denaturing temperature in order to selectively amplify target sequences. Thus Molloy is applicable only for those target sequences having a lower melting temperature (Tm) than their wild-type sequence.

Nucleic acids in cancerous tissues, circulating cells, and cell-free (cf) nucleic acids present in bodily fluids can aid in identifying and selecting individuals with cancer or other diseases associated with such genetic alterations. Mutations in BRAF and KRAS are examples of genetic alterations that confer a survival and growth advantage to cancer cells. Such genetic alterations can be used for selection of targeted therapies. But in a subject, the alterations are present with a large excess of non-altered, wildtype sequences.

See, e.g., Spindler et al., 2012; Benesova et al., 2013; Dawson et al., 2013; Forshew et al., 2012; Shaw et al., 2012. Some data suggest that the amount of mutant DNA in blood correlates with tumor burden and can be used to identify the emergence of resistant mutations (Forshew et al., 2012; Murtaza et al., 2013; Dawson et al., 2013; Diaz et al., 2012; Misale et al., 2012; Diehl et al., 2008).

There is a need for additional methods whereby a greater sensitivity and/or enrichment of target sequence can be achieved with efficiency and ease. The present invention addresses that need.

SUMMARY OF THE DISCLOSURE

The instant disclosure is based in part on the development of a method for substantially enriching for and detecting low-abundance nucleic acid sequences (target sequence) such as altered, mutant, non-wildtype nucleic acid sequence or other nucleic acid not normally present in a biological sample having a background of native nucleic acid, DNA, or RNA sequence, that utilizes fewer steps and greatly reduced reaction assay times while still allowing for orders of magnitude greater sensitivity in detecting a low-abundance nucleic acid sequence. The method is developed to enable enrichment of mutant sequences present in a short, fragmented form (<50 bp) and is also applicable for amplification of less fragmented sequences (>50 bp). Application of the present method allows for enrichment of low-abundance nucleic acid sequence within a high background of non-target or wildtype nucleic acid such that as few as a single copy of target sequence can be detected within a biological sample. The enrichment is based on a relative increase in the amount of the target sequence, via its preferential amplification and thus substantially greater (700×-10000× fold and greater) enrichment relative to other nucleic acids present within the same biological sample.

In a first aspect, the disclosure provides a method for enriching a target nucleic acid sequence in an amplification reaction mixture. The method may comprise a) preparing an amplification reaction mixture comprising a nucleic acid sample comprising a reference (optionally wild-type) sequence and at least suspected of having one or more target (optionally mutant) sequences that are at least 50% homologous to the reference sequence and are also amplifiable by the same primer pair as the reference sequence, and an excess amount of reference blocking nucleic acid sequence which is fully complementary with at least a portion of the sequence of one of the strands of the reference sequence between its primer sites;

b) increasing the temperature of the reaction mixture to a first denaturing temperature that is above the melting temperature (Tm) of the reference sequence and above the melting temperature (Tm) of the double stranded target sequence so as to form denatured reference strands and denatured target strands;

c) reducing the temperature of the reaction mixture so as to permit formation of duplexes of the reference blocking sequence and the complementary reference strand and heteroduplexes of the reference blocking sequence and target strands;

d) increasing the temperature of the reaction mixture to a critical temperature (Tc) sufficient to permit preferential denaturation of said heteroduplexes of the reference blocking sequence and target strands in preference to denaturation of the duplexes of the reference blocking sequence and reference strands;

e) reducing the temperature of the reaction mixture so as to permit the primer pair to anneal to denatured target strands and any denatured reference strands in the reaction mixture;

f) increasing the temperature of the reaction mixture to a denaturing temperature that is above the melting temperature (Tm) of the reference sequence and above the melting temperature (Tm) of the double stranded target sequence so as to form denatured reference strands and denatured target strands to extend the primers annealed to the denatured target strands and denatured reference strands in the reaction mixture; and g) repeating c) through f) for two or more cycles to enrich, in the reaction mixture, the target sequence relative to the reference sequence.

The temperature increase in subparagraph f) is performed without maintenance of any one temperature as a discrete "step" for extension of the annealed primers. Stated differently, the temperature of the reaction mixture is continually increased, after reaching the temperature of subparagraph e), until reaching the denaturing temperature in f). Optionally, the denaturing temperature of subparagraph f) is the same as that in b). Thus in some embodiments, the actions in subparagraphs f) and g) are replaced by the act of repeating b) through e) for two or more cycles to enrich, in the reaction mixture, the target sequence relative to the reference sequence.

The instant disclosure also provides an allele specific competitive cycling assay (ASCC) design based on kinetics of an amplicon and/or a target sequence allowing for a two-step, a three-step or a four-step amplification cycle which reduces method reaction times while substantially enriching for and detecting low-abundance nucleic acid sequence (target sequence) contained in a high background of non-target nucleic acid sequence.

The instant disclosure also provides an allele specific competitive cycling assay (ASCC) design for short amplicons (<50 bp), also suitable for large amplicons (>50 bp) based on a reference blocker oligonucleotide and primer binding kinetics. A reference blocker is a short blocker sequence, allowing for a two-step, a three-step or a four-step amplification cycle, which reduces method reaction times while substantially enriching for and detecting low-abundance nucleic acid sequence (target sequence) contained in a high background of non-target nucleic acid sequence.

The instant disclosure is also based in part on the discovery that for short amplicons, a significant differential in melting temperature can be obtained between reference blocker-reference sequence Tm and reference blocker-target sequence Tm due to a mismatch at the position with variable sequence. Thus, the instant disclosure also provides a method for enriching and detecting low-abundance nucleic acid sequences (target sequence) utilizing short reference blockers of about 80 bp or less or about 60 bp or less, or 40 bp or less or about between 12 to 35 bp in length. Further, the disclosure provides a quantitative method for substantially enriching for and detecting low-abundance nucleic acid sequence (target) present in a sample having a greater abundance of non-target sequence such as native, wild-type, or reference sequence.

The substantially enriched target nucleic acid sequence may be used to provide high detection sensitivity for monitoring or detecting a cancer in a patient by detecting or quantifying the presence of a mutant nucleic acid sequence (e.g. target sequence) in the patient. Target sequence includes, for example, cancer-associated mutant forms of BRAF, EGFR, c-MET, HER-2, HER-3, NRAS, KRAS, PIK3CA, AKT-1, MAP2PK, ER, AR, FGFR1, FGFR2, FGFR3, KIT, PDGFR1, PDFGR2, PDGFR3, TP53, SMAD1 and others.

Also included is a method for using cell-free DNA (cfDNA) that substantially enriches for low levels of target sequence in samples obtained using less-invasive patient sampling methods.

In one aspect, a method for enriching a target nucleic acid sequence in a nucleic acid sample suspected of containing one or more low abundance target sequence is provided, the method comprising:

a. preparing a reaction mixture comprising: a reference sequence, an excess of blocking sequence relative to the amount of reference sequence in the mixture, and suspected of containing one or more target sequence, wherein:
  the target sequence is at least 50% homologous to the reference sequence;
  the blocking sequence is fully complementary with region of the reference sequence, the region of the reference sequence being between or overlapping the target sequence;

b. subjecting the reaction mixture to two or more cycles of:
  i. heating the temperature of the reaction mixture to a preselected denaturation temperature ($T_{sd}$) allowing but not requiring denaturation of blocker sequences annealed to reference sequence, wherein the $T_{sd}$ is above a calculated melting temperature of the reference sequence-blocker sequence duplex, and
  ii. lowering the temperature of the reaction mixture to an elongation temperature allowing primer anneal and elongation of the one or more primer from its complementary target sequence to form enriched target sequence.

In another aspect, a method for enriching a target nucleic acid sequence in a sample suspected of having one or more low abundance target sequence is provided, the method comprising:

a) preparing a reaction mixture including a reference sequence, an excess of blocking sequence that is fully complementary to the reference sequence, and a primer pair that is fully complementary with a region of the target sequence wherein the target sequence has at least 50% complementarity to the reference sequence and subjecting the reaction mixture to two or more cycles of:
  i) a selective temperature ($T_{sd}$) that is above the melting temperature of the target sequence and below the melting temperature of reference sequence homoduplex or blocker-reference sequence duplex so as to allow denaturation of target sequence homoduplex; and
  ii) reducing the temperature of the reaction mixture to a temperature that is above the melting temperature of a blocker-target duplex so as to allow extension of primer:target sequences and enrichment of target sequence relative to the reference sequence in the reaction mixture.

In another aspect, a method for enriching a target nucleic acid sequence in a sample suspected of having one or more low abundance target sequence is provided, the method comprising:
  a) preparing a reaction mixture including a reference sequence, an excess of blocking sequence that is fully complementary to the reference sequence, and a primer pair that is fully complementary with a region of the target sequence between or overlapping the reference sequence, wherein the target sequence has at least 50% complementarity to the reference sequence and subjecting the reaction mixture to two or more cycles of:
  i) heating the reaction mixture to a first temperature sufficient to allow denaturation of homoduplexed reference and target sequences;
  ii) cooling the reaction mixture to a temperature that allows preferential formation of reference-blocker duplexed sequences relative to target-blocker duplexed sequences;
  iii) heating the reaction mixture to a selective denaturation temperature ($T_{sd}$) so as to allow denaturation of the blocker-target duplexed sequences; and
  iv) cooling the reaction mixture to a temperature that is below the melting temperatures of the blocker-reference sequence; the primer pair; and the blocker-mutant sequence so as to allow elongation of primer sequences annealed to the target sequence and substantial enrichment of target sequence relative to reference sequence in the reaction mixture.

Optionally, a blocker:mutant sequence may have a melting temperature that is lower than the reaction temperature of step iv above.

In another aspect, a method for optimizing the design of primer sequences allowing for preferential amplification and substantially greater enrichment of a low-abundance target sequence is provided. Also provided are single-stranded oligonucleotide DNA primers for amplification of a low-abundance target sequence present in sample having a majority background of reference, native, or wild-type nucleic acid.

In one embodiment, the temperature selected for selective denaturation ($T_{sd}$) may be at or above the melting temperature of a target sequence.

In another embodiment, the temperature selected for selective denaturation ($T_{sd}$) may be substantially above the melting temperature of the target sequence.

In another embodiment, the temperature selected for selective denaturation ($T_{sd}$) may be below the melting temperature of target sequence.

The reference blocking sequence, or short blocking sequence may be complementary to a portion of the denatured target strand that is itself also complementary to at least a portion of the 3' end of one or both of the primers used.

The reference blocking oligonucleotide may include a 3'-end that is blocked to inhibit extension. Optionally, the 5'end of the same oligonucleotide may also be blocked. As a non-limiting example, the reference blocking oligonucleotide strand(s) may include a 5'-end comprising a nucleotide that prevents 5' to 3' exonucleolysis by Taq DNA polymerases. In yet additional embodiments, the reference blocking sequence may be a single-stranded nucleic acid reference blocking sequence; a double-stranded nucleic acid reference blocking sequence which denatures to form single strand reference blocking sequences in b) when the reaction mixture is heated to the first denaturing temperature; single stranded DNA, RNA, peptide nucleic acid or locked nucleic acid; or a chimera between single stranded DNA, RNA, peptide nucleic acid or locked nucleic acid or another modified nucleotide.

In some cases, the reference blocking oligonucleotide may contain DNA residues with one or more locked nucleic acid (LNA) nucleotides having a ribose sugar moiety that is "locked" in the 3'-endo conformation. The use of such an LNA reference blocking oligonucleotide may be used to increase the melting temperature of the oligonucleotide for both a reference sequence and target sequence of the disclosure.

In some aspects, the reference blocking oligonucleotide may comprise a shorter sequence of base pairs wherein the blocking oligonucleotide sequence is complementary or specific to the wildtype (non-target) DNA sequence or allele. Such short sequence oligonucleotides ("short blockers") may be complementary to either the forward or reverse strand. Optionally, the short blockers have a melting temperature that is about at or above the melting temperature of its wildtype oligonucleotide sequence. Optionally, there may be some or partial overlap of the blocker sequence with the same-stranded primer sequence. Optionally, the short sequence blocking oligonucleotide may contain LNA(s) as desired. The short sequence is preferably about 80 bp in length or less, or about 60 bp in length or less, or about 40 bp in length or less, or between about 12 to about 60 bp in length.

In some cases of a peptide nucleic acid or LNA, the position(s) of the peptide nucleic acid or locked nucleotide on the chimeric blocking oligonucleotide are selected to match position(s) where mutations are suspected or known to be present, thereby increasing the difference between the temperature needed to denature heteroduplexes of the reference blocking sequence and target strands and the temperature needed to denature heteroduplexes of the reference blocking sequence and the complementary reference strand.

In other embodiments, the reference blocking sequence is fully complementary with one of the strands of the reference sequence between its primer binding sites, or overlapping at either end with the primer binding sites. In further embodiments, the reference blocking sequence is equal to or shorter than the reference sequence. In yet additional embodiments, the reference blocking sequence is present in the reaction mixture at molar excess in comparison to the primers of the primer pair. In other versions, the melting temperature of the double-stranded target sequence is greater than or equal to the melting temperature of the double-stranded reference sequence. In additional versions, the Tsd is maintained for a period from 1 second to 60 seconds.

In another aspect, the method includes use of a reaction mixture comprising a nucleic acid sample having a reference sequence and suspected of having one or more target sequence that are at least 50% homologous to the reference sequence and are also amplifiable by the same primer pair as the reference sequence, an excess amount of blocking nucleic acid sequence. In another aspect, primer sequence is complementary to reference sequence and also contains tag sequences for integration with subsequent mutation detection methods including but not limited to next generation sequencing.

Included in the disclosure are methods wherein the reference and target sequences are first amplified by subjecting the reaction mixture to PCR and then subjecting at least a portion of the reaction mixture to the enrichment method described above. In some cases, the first amplification by PCR may be for 10 cycles or less, 8 cycles or less, or 6 cycles or less. In other cases, the first amplification by PCR may be for 10 cycles or more.

In another embodiment, the target sequence may be that of a homozygous mutation in a subject, such as a human patient. In some cases, the reference and target sequences are KRAS sequences, optionally human KRAS sequences. In other embodiments, the target sequence may contain a mutation in the BRAF sequence. In some cases, the mutation is in a human BRAF sequence. Optionally, the mutation may be the V600E, V600K, V600D, or V600R mutation known to the skilled person as a valine mutation at position 600 of the BRAF amino acid sequence.

In one embodiment the target sequence may be a cancer-associated mutant sequence of BRAF, EGFR, c-MET, HER-2, HER-3, NRAS, PIK3CA, KRAS, AKT-1, MAP2PK, ER, AR, FGFR1, FGFR2, FGFR3, KIT, PDGFR1, PDFGR2, PDGFR3, TP53, SMAD1 or other genes.

In another aspect, the reference and target sequences are cell-free DNA (cfDNA), optionally obtained from a bodily fluid such as urine, blood, serum, or plasma.

In some embodiments, a disclosed primer pair are two oligonucleotide primers wherein each contains a sequence at its 3'-end that is complementary to one strand of a duplex target sequence. Additionally, one or both of the oligonucleotide primers contains a heterologous sequence at its 5'-end that is not found in the target sequence. The heterologous sequence may be artificial, synthetic, manmade, or from a source that is exogenous to the target sequence. The use of such a primer converts the target sequence into a chimeric molecule that is artificial and the result of performing the disclosed synthesis of nucleic acid molecules.

In some embodiments, a disclosed enrichment method is used as part of a method for determining the amount of a target sequence in a sample containing a reference sequence is provided. The method for determining may comprise performance of a disclosed enrichment method followed by an assessment or detection method, such as sequencing or massively parallel sequences as non-limiting example, with a sample from a subject and one or more control samples with a known amount of the target sequence to measure the amount of the target sequence; and then calculating the amount of the target sequence relative to the one or more control samples by comparison to the measurement(s) of one or more known samples of target sequence in the sample. In some cases, the sample is urine, and the target sequence is cfDNA.

DETAILED DESCRIPTION OF THE INVENTION

Figure 1:
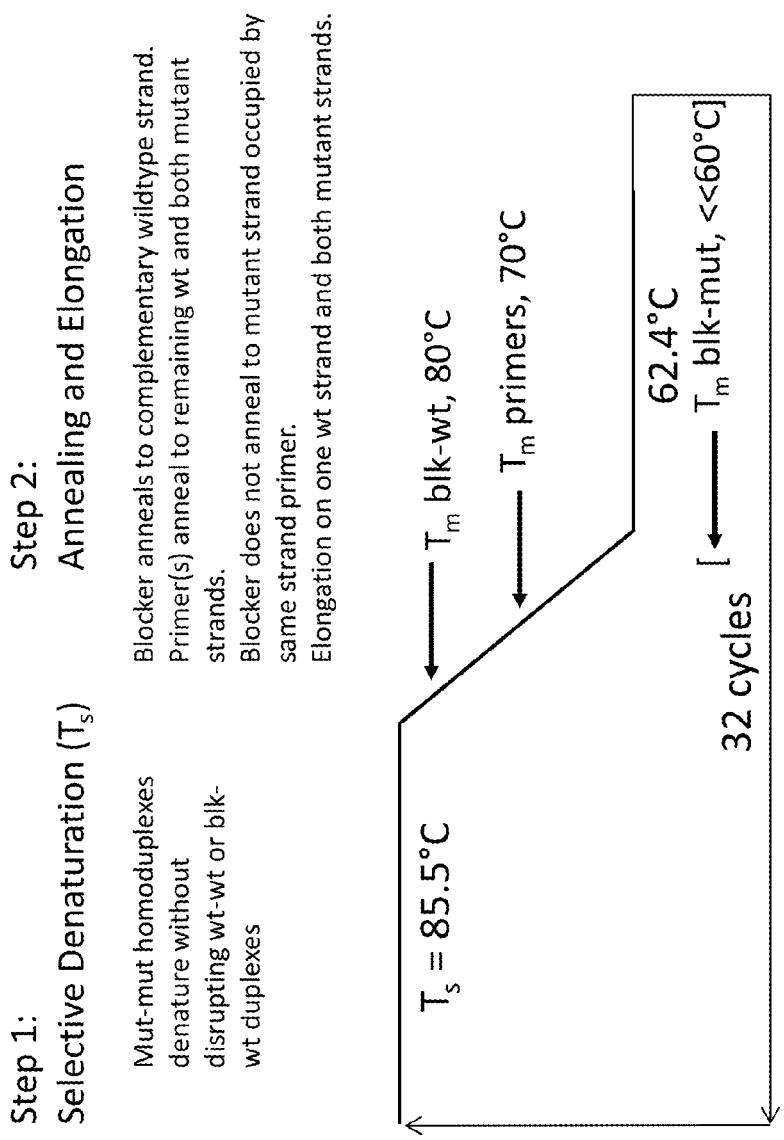
FIG. 1 illustrates one embodiment of the present method.

The present invention is directed to methods, compositions, software and kits for high enrichment of low abundance target nucleic acid sequences from a cell-free sample. The method is based in part on a nucleic acid sequence amplification protocol that is more efficient, has fewer steps and requires shorter reaction times than previous methods. The disclosed method allows orders of magnitude (700×-1000×+) greater detection sensitivity while maintaining target specificity. Unlike prior methods, disclosed herein are methods which employ optimized blocker sequence and primer design as well as requiring far fewer cycle steps. The method provided also allows detection of a greater range of target sequence and is not restricted to identifying only those low-abundance target sequences having a melting temperature that is lower than the melting temperature of the reference sequence.

The present invention can be performed on multiple sample type such as cfDNA (urine, serum, plasma), CTCs, body fluids (saliva, sputum, pancreatic juice, semen, cerebrospinal fluid, tears, mucus) or tissue biopsy (FNA, FFPE, TMA); requires small amounts of tissue or DNA; is quantifiable; has ability to multiplex preferential enrichment of all mutations and detects all mutations in amplified region. The present invention is not restricted to detection of allele-specific mutations).

As used herein, the term "enriching a target sequence" or "enrichment" of a low-abundance target nucleic acid refers to increasing the amount of a target sequence and increasing the ratio of target sequence relative to the corresponding reference sequence in a sample. For example, where the ratio of target sequence to reference sequence is initially 5% to 95% in a sample, the target sequence may be preferentially amplified in an amplification reaction so as to produce a final ratio of 99.99999% and 0.00001% reference sequence, or the target sequence may be preferentially amplified in an amplification reaction so as to increase its presence within the sample by orders of magnitude. For example, where there may be at least 1 strand of target sequence within an original sample of an amplification reaction mixture, there will be 100 to 11000 strands or greater of target sequence present in the amplification reaction mixture subsequent to amplification, thus a 100× to at least 11000× or greater enrichment of the target sequence relative to the quantity of reference sequence in the original sample.

As used herein, the term "target sequence" refers to a nucleic acid that is in low-abundance or is less prevalent in a nucleic acid sample than a corresponding reference sequence. The target sequence will make up less than 50% of the total amount of reference sequence+target sequence in a sample. The target sequence may be an abnormal or mutant allele. For example, a sample (e.g. tissue, blood, plasma, urine or other bodily fluid) may contain numerous normal cells and few or a single cancerous cell. The normal cells contain non-mutant or wild-type alleles, while the cancerous cells contain somatic mutations and/or differences in sequence as compared to their counterpart non-mutant or wild-type allele. In such a case, the mutant is the target sequence while the wild-type sequence is the reference sequence. As used herein, a "target strand" refers to a single nucleic acid strand of a double-stranded target sequence.

The target sequence must be at least 50% homologous to the corresponding reference sequence, but must differ by at least one nucleotide from the reference sequence. Target sequences are amplifiable via PCR with the same pair of primers as those used for the reference sequence but need not be so restricted. Target sequences may also be amplifiable via PCR with primer pairs not used for the reference sequence so long as the primers are selected to amplify at region of sequence containing the target sequence.

As used herein, the term "amplicon" refers to a nucleic acid that is the product of amplification. Thus an amplicon may be homologous to a reference sequence, a target sequence, or any sequence of nucleic acid that has been subjected to amplification. Generally, within a reaction sample, the concentration of amplicon sequence will be significantly greater than the concentration of original (template) nucleic acid sequence.

As used herein, the term "reference sequence" refers to a nucleic acid that is more prevalent in a nucleic acid sample than a corresponding target sequence. The reference sequence makes-up over 50% of the total reference sequence+target sequence in a sample. Preferably the reference sequence is expressed at the DNA and/or RNA level 10×, 15×, 20×, 25×, 30×, 35×, 40×, 45×, 50×, 60×, 70×, 80×, 90×100×, 150×, 200× or more than the target sequence. As used herein, a "reference strand" refers to a single nucleic acid strand of a double-stranded reference sequence.

As used herein, the term "wild-type" refers to the most common polynucleotide sequence or allele for a certain gene in a population. Generally, the wild-type allele will be obtained from normal cells. Depending on the particular purpose or desire of the practitioner, the reference sequence is generally a wild-type sequence.

As used herein, the term "mutant" refers to a nucleotide change (i.e., a single or multiple nucleotide substitution, deletion, or insertion) in a nucleic acid sequence. A nucleic acid which bears a mutation has a nucleic acid sequence (mutant allele) that is different in sequence from that of the corresponding wild-type polynucleotide sequence. The invention is broadly concerned with somatic mutations and polymorphisms. The methods of the invention are especially useful in selectively enriching a mutant allele which contains between about 1 and 10 nucleotide sequence changes, although it is useful even with a higher number of sequence changes. A mutant allele will typically be obtained from diseased tissues or cells and is associated with a disease state.

As used herein the term "melting temperature" or "$T_m$" refers to the temperature at which a polynucleotide dissociates from its complementary sequence. Generally, the $T_m$ may be defined as the temperature at which one-half of the Watson-Crick base pairs in a double stranded nucleic acid molecule are broken or dissociated (i.e., are "melted") while the other half of the Watson-Crick base pairs remain intact in a double stranded conformation. In other words the $T_m$ is defined as the temperature at which 50% of the nucleotides of two complementary sequences are annealed (double strands) and 50% of the nucleotides are denatured (single strands). $T_m$, therefore defines a midpoint in the transition from double-stranded to single-stranded nucleic acid molecules (or, conversely, in the transition from single-stranded to double-stranded nucleic acid molecules).

A "selected denaturation temperature" or "$T_{sd}$" is a temperature determined utilizing a preselected design including parameters and calculated $T_m$ according to one aspect of an embodiment as disclosed herein. Generally, in the method provided herein, a selected temperature will be a preselected temperature that is below the melting temperature of a blocker:reference sequence, or above the melting temperature of a blocker:reference sequence or about at the melting temperature of a blocker:reference sequence.

The $T_m$ can be estimated by a number of methods, for example by a nearest-neighbor calculation as per Wetmur 1991 (Wetmur, J. G. 1991. DNA probes: applications of the principles of nucleic acid hybridization. Crit Rev Biochem Mol Biol 26: 227-259,) and by commercial programs including Oligo™ Primer Design and programs available on the internet. Alternatively, the $T_m$ can be determined though actual experimentation. For example, double-stranded DNA binding or intercalating dyes, such as Ethidium bromide or SYBR-green (Molecular Probes) can be used in a melting curve assay to determine the actual $T_m$ of the nucleic acid. Additional methods for determining the $T_m$ of a nucleic acid are well known in the art. Some of these methods are listed in the inventor's prior patent application entitled "Enrichment of a Target Sequence", International Application No. PCT/US2008/009248, now U.S. Ser. No. 12/671,295, incorporated by reference herein.

As used herein, "reference blocking sequence" is an engineered single stranded or double stranded nucleic acid sequence, such as an oligonucleotide and preferably has a length smaller than the amplified section of the target sequence. In one embodiment, the reference blocking sequence is several bases smaller than the amplified section of the reference sequence, on each side of the sequence so that the primers do not bind appreciably to the reference sequence. In another embodiment, the reference blocking sequence may overlap with a primer binding site. Optionally, the 3' OH end of the reference blocking sequence is blocked to DNA-polymerase extension. Optionally, the 5'-end is modified to prevent 5' to 3' exonucleolysis by Taq DNA polymerases. The reference blocking sequence can also take other forms which remain annealed to the reference sequence when the reaction mixture is subject to the critical temperature "$T_c$", such as a chimera between single stranded DNA, RNA, peptide nucleic acid (PNA) or locked nucleic acid (LNA), or another modified nucleotide.

In one embodiment, a PNA or LNA is used in the reference blocking sequence at a positions which flank and/or include the nucleotide in the reference sequence differs from that in the target sequence. Such a construction will increase the difference in the melting temperature of the reference blocking sequence-reference sequence and the reference blocking sequence-target sequence heteroduplexes to further favor denaturation of reference blocking sequence-target sequence heteroduplexes at the $T_{sd}$ and enrichment of the target sequence. Furthermore, PNA or LNA modifications may be added to other positions with the reference blocking sequence as to elevate and adjust the melting temperatures of the reference blocking sequence with the reference sequence and with the target-sequence.

If one or more modified nucleotide, LNA or PNA is present in the reference blocking sequence, the position of the modified nucleotide, LNA or PNA may be selected to match at least one position where a mutation (i.e. a difference in sequence between the target and reference sequences) is suspected to be present. By selecting this position for incorporation of the modified nucleotide in the reference blocking sequence, the difference between the temperature needed to denature duplexes of the reference blocking sequence and the complementary reference strand and that required to denature heteroduplexes of the reference blocking sequence and the partially complementary target sequence is maximized.

A "reference blocking" sequence or "short blocking" sequence or "blocker" sequence may be fully complementary with one strand of the reference sequence (between primer binding sites or partially overlapping the primer binding sites). The reference blocking sequence and short blocking sequence are shorter than the reference sequence. A blocker sequence may exceed the length of a primer. For example, (depending upon a target sequence length) in the case where a blocker sequence fully extends along the length of a forward or a reverse primer including into a sequenced region and includes overlap with a reverse blocker. For example: a KRAS blocker having a 13 base pair forward primer may be 13 nucleotide bases from a forward primer+5 bases in the sequencing region+up to 3 bp complementary to the reverse primer. In this example, a blocker can include a length of about 21 base pair with longer primers and longer sequenced regions extending the total length.

As used herein, "short blocking sequence" or "short blocker" is a reference blocking sequence having 80 bp length or less, or 60 bp length or less, or between 10 bp and 63 bp in length. A short blocker sequence include "hot blocker sequences" or sequences having a melting temperature that is above the melting temperature of the reference sequence or a WT-WT duplex nucleotide strand. Preferably, a short blocking sequence when duplexed with a reference sequence, will have a blocker:reference sequence melting temperature that is greater than the melting temperature of at least one primer of the pair included in a reaction mixture.

A reference blocking sequence or short blocking sequence may also be designed so as to allow amplification of fragments (amplicons) of any size length. Such blocking sequences are preferably designed so as to have a length sufficient to amplify short fragmented nucleic acids such as those fragmented DNA sequences present in a cell-free DNA sample. A reference blocking sequence is preferably designed so as to allow a differential between the melting temperature of blocking sequence-reference sequence and melting temperature of blocking sequence-target sequence and melting temperature of a primer in the reaction mixture. Of course, as would be apparent to one skilled in the art, the length of a reference blocking sequence has no maximum or upper limit as the kinetics of the method are based in part on a relationship between a primer-blocker binding temperature and a native-denatured conformation of a target nucleic acid. A blocker having a high melting temperature and present in excess quantity in a reaction mixture, allows achievement of its preferential binding or annealing to a reference nucleic acid or wildtype nucleic acid sequence. Additionally, where a target:blocker melting temperature is lower or substantially lower due to nucleic acid sequence mismatch it will result in a less favored kinetics or binding rate—allowing the forward or reverse primer to preferentially anneal to the target nucleic acid sequence relative to or as compared to the kinetics or rate of blocker binding/annealing to a target sequence.

A "critical temperature" or "$T_c$" refers to a temperature below the melting temperature "$T_m$" of the reference sequence. In some embodiments, the $T_c$ is below the $T_m$ of both the reference and the target sequence ($T_c < T_{ref}$ or $T_{tgt}$). The critical temperature takes advantage that at a temperature lower than $T_m$, a double stranded target sequence and target-reference sequence (bl:ref) cross hybridized to form double stranded DNA duplex so as to preferentially denature these heteroduplexes over the reference/reference homoduplexes. When the target sequence and reference sequence cross hybridize, minor sequence differences of one or more single nucleotide mismatch anywhere along a short (e.g., <200 bp) double stranded DNA sequence will generate a predictable change in the melting temperature ($T_m$) for that sequence (Lipsky, R. H., et al. (2001) *Clin Chem*, 47, 635-644; Liew, M., et al. (2004) *Clin Chem*, 50, 1156-1164). Depending on the exact sequence context and position of the mismatch, melting temperature changes of 0.1-20° C., are contemplated.

A "primer sequence" includes nucleic acid sequences of 9-30 bp, or 10-25 bp, or 11-22 bp or 13-16 bp in length. A primer sequence is a synthetically engineered nucleic acid sequence that anneal to opposite strands of a target and reference sequence so as to form an amplification product during a PCR reaction. The target and the reference sequence should be at least 25 bases in order to facilitate primer attachment. A primer sequence may include tag or adapter sequence. Adapters are engineered nucleic acid which may be 15-30 bp, or 20-25 bp, or 18-23 bp in length. The primer pair may be designed so as to have a $T_m$ lower than the $T_{sd}$ of the reaction. As used herein, "primer pair" refers to two primer sequences designed so as to anneal to and extend from complementary nucleic acid strands and may be up to 45 bp.

As used herein, "homology" refers to the subunit sequence similarity between two polymeric molecules, e.g., two polynucleotides or two polypeptides. An example of an algorithm that is suitable for determining percent sequence identity and sequence similarity are the BLAST and BLAST 2.0 algorithms, which are described in Altschul et al., Nuc. Acids Res. 25:3389-3402 (1977) and Altschul et al., J. Mol. Biol. 215:403-410 (1990), respectively.

The disclosure provides a sensitive, easy and inexpensive test for the routine clinical detection of a gene alteration in cell-free nucleic acids from a sample of a subject. In some embodiments, the test is based on KRAS mutant detection. In other embodiments, the test may be for a BRAF mutation, such as the BRAF V600E mutation or an EGFR mutation, c-met, MET, HER-2, HER-3, NRAS, PIK3CA 1047, KRAS 161H and others. In other embodiments, the gene alteration may be a substitution, insertion, deletion, or translocation resulting in a difference between a target sequence and the corresponding reference sequence.

In addition to particular mutations described herein, the disclosure provides for the use of the disclosed methods for any cellular or mitochondrial mutation associated with a disease or disorder in the presence of wildtype sequences. In many embodiments, the disclosed methods may be performed in cases of cancer, including primary cancer or cancer that has metastasized. In other cases, the methods may be used in cases of a malignant, or non-malignant, tumor.

Non-limiting examples of cancer include, but are not limited to, adrenal cortical cancer, anal cancer, bile duct cancer, bladder cancer, bone cancer, brain or a nervous system cancer, breast cancer, cervical cancer, colon cancer, recta; cancer, colorectal cancer, endometrial cancer, esophageal cancer, Ewing family of tumor, eye cancer, gallbladder cancer, gastrointestinal carcinoid cancer, gastrointestinal stromal cancer, Hodgkin Disease, intestinal cancer, Kaposi Sarcoma, kidney cancer, large intestine cancer, laryngeal cancer, hypopharyngeal cancer, laryngeal and hypopharyngeal cancer, leukemia, acute lymphocytic leukemia (ALL), acute myeloid leukemia (AML), chronic lymphocytic leukemia (CLL), chronic myeloid leukemia (CML), chronic myelomonocytic leukemia (CMML), non-HCL lymphoid malignancy (hairy cell variant, splenic marginal zone lymphoma (SMZL), splenic diffuse red pulp small B-cell lymphoma (SDRPSBCL), chronic lymphocytic leukemia (CLL), prolymphocytic leukemia, low grade lymphoma, systemic mastocytosis, or splenic lymphoma/leukemia unclassifiable (SLLU)), liver cancer, lung cancer, non-small cell lung cancer, small cell lung cancer, lung carcinoid tumor, lymphoma, lymphoma of the skin, malignant mesothelioma, multiple myeloma, nasal cavity cancer, paranasal sinus cancer, nasal cavity and paranasal sinus cancer, nasopharyngeal cancer, neuroblastoma, non-Hodgkin lymphoma, oral cavity cancer, oropharyngeal cancer, oral cavity and oropharyngeal cancer, osteosarcoma, ovarian cancer, pancreatic cancer, penile cancer, pituitary tumor, prostate cancer, retinoblastoma, rhabdomyosarcoma, salivary gland cancer, sarcoma, adult soft tissue sarcoma, skin cancer, basal cell skin cancer, squamous cell skin cancer, basal and squamous cell skin cancer, melanoma, uveal melanoma, stomach cancer, small intestine cancer, testicular cancer, thymus cancer, thyroid cancer, uterine sarcoma, uterine cancer, vaginal cancer, vulvar cancer, Waldenstrom Macroglobulinemia, and Wilms Tumor.

Non-limiting examples of non-HCL lymphoid malignancy include, but are not limited to, hairy cell variant (HCL-v), splenic marginal zone lymphoma (SMZL), splenic diffuse red pulp small B-cell lymphoma (SDRPSBCL), splenic leukemia/lymphoma unclassifiable (SLLU), chronic lymphocytic leukemia (CLL), prolymphocytic leukemia, low grade lymphoma, systemic mastocytosis, and splenic lymphoma/leukemia unclassifiable (SLLU).

As used herein, a "patient" includes a mammal. The mammal can be e.g., any mammal, e.g., a human, primate, bird, mouse, rat, fowl, dog, cat, cow, horse, goat, camel, sheep or a pig. In many cases, the mammal is a human being.

In additional embodiments, the disclosed methods are used with human subjects, such as those undergoing therapy or treatment for a disease or disorder associated with a gene alteration as described herein, or subjects surveyed for residual disease or recurrence. Subjects may be any individual of any age, sex or race.

In many cases, the sample from a subject, and containing a target sequence, is a bodily fluid. Non-limiting examples of a bodily fluid include, but are not limited to, peripheral blood, serum, plasma, urine, sputum, saliva, pancreatic juice, cerebrospinal fluid, tears, mucus, semen, lymph fluid, amniotic fluid, and spinal fluid. The disclosure demonstrates that substantial (100×-11000× fold) enrichment of target sequence can be achieved thereby allowing for down to single-copy mutant sequence (e.g. EGFR deletion, EGFR T790M, KRAS single base substitution), within a biological sample containing a background of non-target nucleic acid can be detected. The disclosure also demonstrates that massively parallel sequencing can be an effective tool to monitor mutation status of the KRAS gene in urinary cfDNA. The assay is selective and highly specific for all seven KRAS mutations within KRAS codons 12 and 13. Results show that mutated KRAS could be detected in the urine of 8 out of 9 patients whose tumor tissue contained a KRAS mutation. The discrepancy of the called nucleotide in 4 of the 8 detectable tumor samples may highlight discrepancies in patient tumor heterogeneity of these samples. Using massively parallel DNA sequencing to detect mutations from cell-free urinary DNA non-invasively monitors metastatic patients for response, non-response and the emergence of resistance mechanisms of molecularly targeted therapies.

As used herein, the term "sample" refers to anything which may contain an analyte for which an analyte assay is desired. In many cases, the analyte is a cell-free (cf) nucleic acid molecule, such as a DNA or cDNA molecule encoding all or part of BRAF. The term "sample" includes a sample of nucleic acid (genomic DNA, cDNA, RNA, mRNA). The sample may be a biological sample, such as a biological fluid or a biological tissue. Examples of biological fluids include urine, blood, plasma, serum, saliva, pancreatic juice, semen, stool, sputum, cerebrospinal fluid, tears, mucus, amniotic fluid or the like. Biological tissues are aggregates of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s). A "sample" also includes a sample of in vitro cell culture constituents, natural isolates (such as drinking water, seawater, solid materials), microbial specimens or specimens that have been "spiked" with nucleic acid tracer molecules.

Nucleic acid sequences of the invention can be amplified from genomic DNA. Genomic DNA can be isolated from tissues or cells according to the following method or an alternative method. Such methods are well known in the art. Alternatively nucleic acids sequences of the invention can be isolated from blood or another fluid by methods well known in the art.

In some embodiments, a disclosed enrichment method is used as part of a method for determining the amount of a target sequence in a sample containing a reference sequence. The enrichment method may also be combined with a detection method for assessing one or more mutations post-enrichment. The method may comprise performance of a disclosed enrichment method followed by an additional assessment or detection method, such as sequencing or massively parallel sequences as non-limiting example, with a sample from a subject and one or more control samples with a known amount of the target sequence to measure the amount of the target sequence; and then calculating the amount of the target sequence and the one or more control samples by comparison to the measurement(s) of one or more known samples of target sequence in the sample. The disclosed methods may further include analyzing the reaction mixture with enriched target sequence using one or more methods selected from MALDI-TOF, HR-melting, di-deoxy-sequencing, single-molecule sequencing, pyrosequencing, second generation high-throughput sequencing, SSCP, RFLP, dHPLC, CCM, digital PCR and quantitative-PCR. These analytical techniques may be used to detect specific target (mutant) sequences within synthesized nucleic acids as described herein. In some cases, the sample is urine, and the target sequence is cfDNA.

The skilled artisan can determine useful primers for PCR amplification of any mutant sequence for any of the methods described herein. In some embodiments, the PCR amplifies a sequence of less than about 50 nucleotides, e.g., as described in US Patent Application Publication US/2010/0068711. In other embodiments, the PCR is performed using a blocking oligonucleotide that suppresses amplification of a wildtype version of the gene, e.g., as described in U.S. Pat. No. 8,623,603 or U.S. Provisional Patent Application No. 62/039,905. In some embodiments, one or more primers contains an exogenous or heterologous sequence (such as an adapter or "tag" sequence), as is known in the art, such that the resulting amplified molecule has a sequence that is not naturally occurring.

A disclosed primer pair are two oligonucleotide primers wherein each contains a sequence at its 3'-end that is complementary to one strand of a duplex target sequence. Additionally, one or both of the oligonucleotide primers contains a heterologous sequence at its 5'-end that is not found in the target sequence. The heterologous sequence may be artificial, synthetic, manmade, or from a source that is exogenous to the target sequence. The use of such a primer results converts the target sequence into a chimeric molecule that is artificial and the result of performing the disclosed synthesis of nucleic acid molecules. A primer may be up to 45 bp or about 9-30, 10-25, 11-22 or 13-16 bp in length. A primer may include an adapter sequence. An adapter sequence may be about 15-30 bp, 20-25 bp or 18-23 bp in length.

In one embodiment, the described method may also be performed as a quantitative assay allowing for quantification of the detected target (mutant) sequences. The quantification provides a means for determining a calculated input percentage of the target sequence prior to enrichment based upon the output signal (optionally as a percentage) from the assessment. This may be performed by reference to a fitted curve like those illustrated in FIG. 12. The actual output from an assessment of a test sample is determined in combination with one or more control reactions containing a known quantity of target sequence DNA. The outputs from the test sample and the control(s) are compared to a fitted curve to interpolate or extrapolate a calculated input for the test sample. This permits a quantitative determination of the amount of a target sequence in a sample pre-enrichment based upon a post-enrichment detection.

The detection limits for the presence of a gene alteration (mutation) in cf nucleic acids may be determined by assessing data from one or more negative controls (e.g. from healthy control subjects or verified cell lines) and a plurality of patient samples. Optionally, the limits may be determined based in part on minimizing the percentage of false negatives as being more important than minimizing false positives. One set of non-limiting thresholds for BRAF V600E is defined as less than about 0.05% of the mutation in a sample of cf nucleic acids for a determination of no mutant present or wild-type only; the range of about 0.05% to about 0.107% as "borderline", and greater than about 0.107% as detected mutation. In other embodiments, a no-detection designation threshold for the mutation is set at less than about 0.1%, less than about 0.15%, less than about 0.2%, less than about 0.3%, less than about 0.4%, less than about 0.5%, less than about 0.6%, less than about 0.7%, less than about 0.8%, less than about 0.9%, or less than about 1% detection of the mutation relative to a corresponding wild-type sequence. One set of non-limiting thresholds for KRAS Exon 2 mutation assay is defined as less than 1 copy of the mutation for quantitative determination of mutation.

Prior PCR Methods of Enrichment

Prior PCR-based methods of enrichment for low-abundance target sequence (e.g., full or fast COLD-PCR) employ standard amplification protocols and are based solely on the theoretical difference in melting temperature between the double stranded reference sequence and the double stranded target sequence. For example in Molloy et al., International Application Publication No. WO/03/072809, Melting Temperature Dependent DNA Amplification, they discovered that selective amplification of a nucleic acid can be achieved by varying the denaturation temperature. The method preferentially amplifies a sequence having a lower denaturation temperature (typically the mutant sequence) than that of the reference sequence by cycling the denaturation temperature at or above the melting temperature of the target temperature but below the reference temperature. In another example, example, in International Application No. PCT/US2008/009248, now U.S. Ser. No. 12/671,295, by Makrigiorgos et al., Full COLD-PCR, after a first denaturation chosen to be "well above" the Tm for the reference and target sequences, the reaction mixture is cooled over an 8 minute time period and then incubated at a critical denaturing temperature (Tc), "chosen to be less than the melting temperature for the double stranded reference sequence and higher than the lower melting temperature of the reference-target heteroduplexes." (See, Description of Invention). With Fast COLD-PCR, the reaction mixture is not subjected to a first denaturation at a temperature above the reference sequence Tm (e.g. 94.C.), but instead, is incubated at a critical denaturing temperature (e.g., $T_c$=83.5° C.), which is chosen either (a) to be less than the melting temperature for the double stranded reference sequence and higher than the lower melting temperature of the double stranded target sequence, or; (b) to be lower than the $T_m$ of both reference and target sequences, whilst still creating a differential between the degree of denaturation of reference and target sequences. (See, Description of the Invention). Full COLD-PCR is described by Makrigiorgos et al. to be "inefficient and "time consuming" and Fast COLD-PCR is unable to detect "mutant sequences having the same or higher than" Tm of the wild-type sequence (See, US20140106362, Background of the Invention). In both U.S. Pat. No. 8,623,603 and US20140106362 by Makrigiorgos et al., ("Full cold-PCR enrichment with reference blocking sequence") attempts to address the problems of Full and Fast COLD-PCR include use of "excess amount of reference blocking sequence" in the reaction mixture to improve efficiency and reduce cycle time. With all prior enrichment methods, because the target sequence melting temperature (Tm) must be lower than the reference sequence melting temperature (Tm), the methods allow detection only of those mutant sequences having a Tm that is lower than the wild-type Tm. Thus, such prior methods are restricted to conditions where the Tm of the double stranded target sequence is lower than the Tm for the double stranded reference sequence. This is true even in Full cold PCR wherein the heteroduplex is formed specifically to create a double-stranded molecule that will have a lower Tm than that of the WT:WT homoduplex molecule. In the present method, because the blocker:reference sequence can be any of the three categories (above, below or at the Tm) our method is effective independent of the melting temperature of the PCR product. Enrichment becomes independent of the melting temperature, utilizing advantageous aspects of short amplicon binding kinetics between a blocker and a reference or blocker and target strand; an aspect independent of prior methods.

The present disclosure provides a method that allows detection of a greater range of target sequence and is not limited to identification of only those target sequences having a melting temperature that is lower than the reference sequence melting temperature.

The present method allows for a substantially greater (700×-1000×) enrichment of low-abundance nucleic acid sequence within a sample and particularly a sample containing fragmented DNA and/or containing a majority of wild-type or non-target sequence. For example, a single copy mutation in high background (e.g., 10,000 or greater) wild type molecules. After performance of the method, the ratio of target molecule vs reference becomes substantially increased Fast/Differential Kinetic Blocker The methods provided herein employ sets of amplification cycles utilizing specifically designed reference blocker sequence and primer sequence. The blocker sequences are a short nucleotide sequence having complementarity to a selected original or wild-type nucleotide sequence. Optionally, the short blockers include LNAs as predetermined or desired by the practitioner. Short blocker sequence may be complementary to either the forward or reverse strand are preferably are preselected based upon a design method provided herein and below. If desired, there may be overlap of the blocker sequence with the same-stranded primer.

The methods described herein include more than one set of amplification cycles. A set of amplification cycles may include 2 or more amplification cycles, 3 or more amplification cycles, suitably 5 or more amplification cycles, suitably 7 or more amplification cycles, suitably 10 or more amplification cycles. A set of amplification cycles may include 2-30 cycles, 4-25 cycles, 5-20 cycles, or 40 cycles or greater.

With the fast or differential kinetic blocker methods described herein, the target and reference sequences in the nucleic acid sample may but need not be amplified by a pre-amplification method such as PCR prior to inclusion in the methods. The PCR may be completed by using the first denaturing temperature that is higher than the melting temperature of a reference sequence such that both the reference sequence and the target sequence are amplified. Reaction mixture including excess blocker may also be used. Excess blocker aids in preventing strand binding and further drives the selective amplification process.

PCR may also be used subsequent to employing a method described herein to further amplify the nucleic acids in the sample after the enrichment procedure. The methods described herein may also be followed by analysis of the amplification reaction mixture using a mutation detection method. Those skilled in the art will appreciate that many methods may be used to analyze a sample for a particular (i.e. target) nucleic acid. Such methods include, but are not limited to, MALDI-TOF, HR-Melting, Di-deoxy-sequencing, Single-molecule sequencing, pyrosequencing, Second generation high-throughput sequencing, SSCP, RFLP, dHPLC, CCM, digital PCR and quantitative-PCR. These methods may be useful for detecting target sequences that represent a mutant allele of the reference sequence comprising a deletion, insertion or alteration of one or more nucleotides.

The methods described herein may be performed in a quantitative or real-time PCR device. The reaction mixture may contain a nucleic acid detection agent, such as a nucleic acid detection dye (e.g., SYBR Green) or a labeled probe (e.g., a TaqMan probe or other oligonucleotide labeled with a fluorescent marker). The methods described herein may also be used to enrich two or more different target sequences and the target sequences may be amplifiable with the same primer pair or with different primer pairs. Such a reaction may include more than one nucleic acid detection agent.

It will be understood by one skilled in the art that any of the methods illustrated or provided herein can and should be optimized for individual protocols, conditions and practitioner objective.

The present disclosure also provides, in part, a kit for performing the disclosed methods. Examples of various chemical reagents to be included in a kit are: packaged in suitable containers—one or more target sequence primer oligonucleotide for amplifying the target nucleic acid, one or more blocker oligonucleotide, a DNA polymerase, a buffer solution for nucleic acid amplification reaction, and control reagents (e.g., positive and/or negative control target nucleic acid and positive and/or negative control wild-type or reference nucleic acid at a standard concentration) and/or instructions for using the kit to detect and optionally quantitate one or more low-abundance target nucleic acid. The kit may also include various chemical reagents or appliances, as well as a unit for detection comprising a solution and/or a substance reactable with a dye, tag, fluorescent label or other such marker; the solution containing a dye which binds to a nucleic acid.

The methods and reagents of the present invention can be conveniently packaged in kit form. Such kits can be used in various research and diagnostic applications as described herein.

One skilled in the art may refer to general reference texts for detailed descriptions of known techniques discussed herein or equivalent techniques. These texts include Ausubel et al., Current Protocols in Molecular Biology, John Wiley and Sons, Inc. (2005); Sambrook et al., Molecular Cloning, A Laboratory Manual (3rd edition), Cold Spring Harbor Press, Cold Spring Harbor, N.Y. (2000); Coligan et al., Current Protocols in Immunology, John Wiley & Sons, N.Y.; Enna et al., Current Protocols in Pharmacology, John Wiley & Sons, N.Y.; Fingl et al., The Pharmacological Basis of Therapeutics (1975), Remington's Pharmaceutical Sciences, Mack Publishing Co., Easton, Pa., 18th edition (1990). These texts can, of course, also be referred to in making or using an aspect of the disclosure.

Preferred embodiments are described in the following examples. Other embodiments within the scope of the claims herein will be apparent to one skilled in the art from consideration of the specification or practice of the invention as disclosed herein. Other features and advantages of the present disclosure are also apparent from the different examples. The provided examples illustrate different components and methodology useful in practicing the present disclosure. It is intended that the specification, together with the examples, be considered exemplary only. The technical scope of the present invention is not limited to these examples.

EXAMPLES

Example 1

An example of a two-step PCR enrichment assay (EGFR Exon 19 deletions) is provided in FIG. 1. In this assay, a selective denaturation step precedes the annealing step. As the reaction ramps to the annealing temperature of 62.4° C., any complementary wildtype strands generated in the previous PCR cycle bind blocker before the primers anneal. The primers then anneal to the complementary mutant strand and bar the possibility of any blocker binding to that mutant strand due to sequence overlap. (For most deletions the likelihood of any blocker binding to the mutant is extremely low as there is actually very little common sequence). In this exemplary assay, at the preselected annealing step (62.4° C.), blocker:target and reference (wt):target heteroduplex formation is likely to be extremely low (below detectable or calculable levels) because only a minor percentage will be complementary.

TABLE 1

Deletion-Specific Cycling Conditons (DSCC-3)

| Step | Temp | Time |
|---|---|---|
| | Lid 98° C. | |
| Stage 1 (32 cycles) | 85.5° C. | 15 s |
| | 62.4° C. | 20 s |
| | 12° C. | Hold |

TABLE 2

Round one ASCC cycling conditions

| Stage | Step | Temp | Time |
|---|---|---|---|
| Initial Denaturation | denature template DNA | 98° C. | 2 min |
| Stage 1 (5 cycles) | denature DNA | 98° C. | 10 sec |
| | anneal primers/extend | 60° C. | 20 sec |
| Stage 2 (30 cycles) | denature DNA | 98° C. | 10 sec |
| | anneal blk-wt; blk-mt; primers remain unbound | 70° C. | 30 sec |
| | denature blk-wt, blk-mt | Tc | 15 sec |
| | anneal wt-blocker, primers, mt/blocker, extend | 60° C. | 20 sec |

TABLE 3

Fold Enrichment by Input and WT Background level - Single MT c.2235_2249del15

| | 10 ng background | 60 ng background | 180 ng background | 360 ng background |
|---|---|---|---|---|
| 10 copies Input | 8997 | 7826 | 3428 | 1878 |
| 5 copies Input | 14172 | 5298 | 3838 | 1544 |
| 3 copies Input | 9056 | 11107 | 2424 | 2231 |

TABLE 4

| Input | Fold Enrichment of Single Mutation c2235_2249del15 |
|---|---|
| 500 | 687 |
| 100 | 1105 |
| 20 | 1047 |
| 10 | 945 |
| 3 | 722 |
| 1 | 1293 |

TABLE 5

Fold Enrichment of Pooled Mutant Sequences

| Input | c2235_2249 | c2236_2250 | c2240_2257 | c2233_2247 |
|---|---|---|---|---|
| 500 | 472 | 525 | 350 | 406 |
| 100 | 863 | 1371 | 899 | 1187 |
| 20 | 1053 | 1189 | 701 | 1089 |
| 10 | 918 | 1318 | 456 | 749 |
| 3 | 1071 | 661 | 543 | 1423 |
| 1 | 567 | 232 | 353 | 1289 |

Example 2

Figure 2:
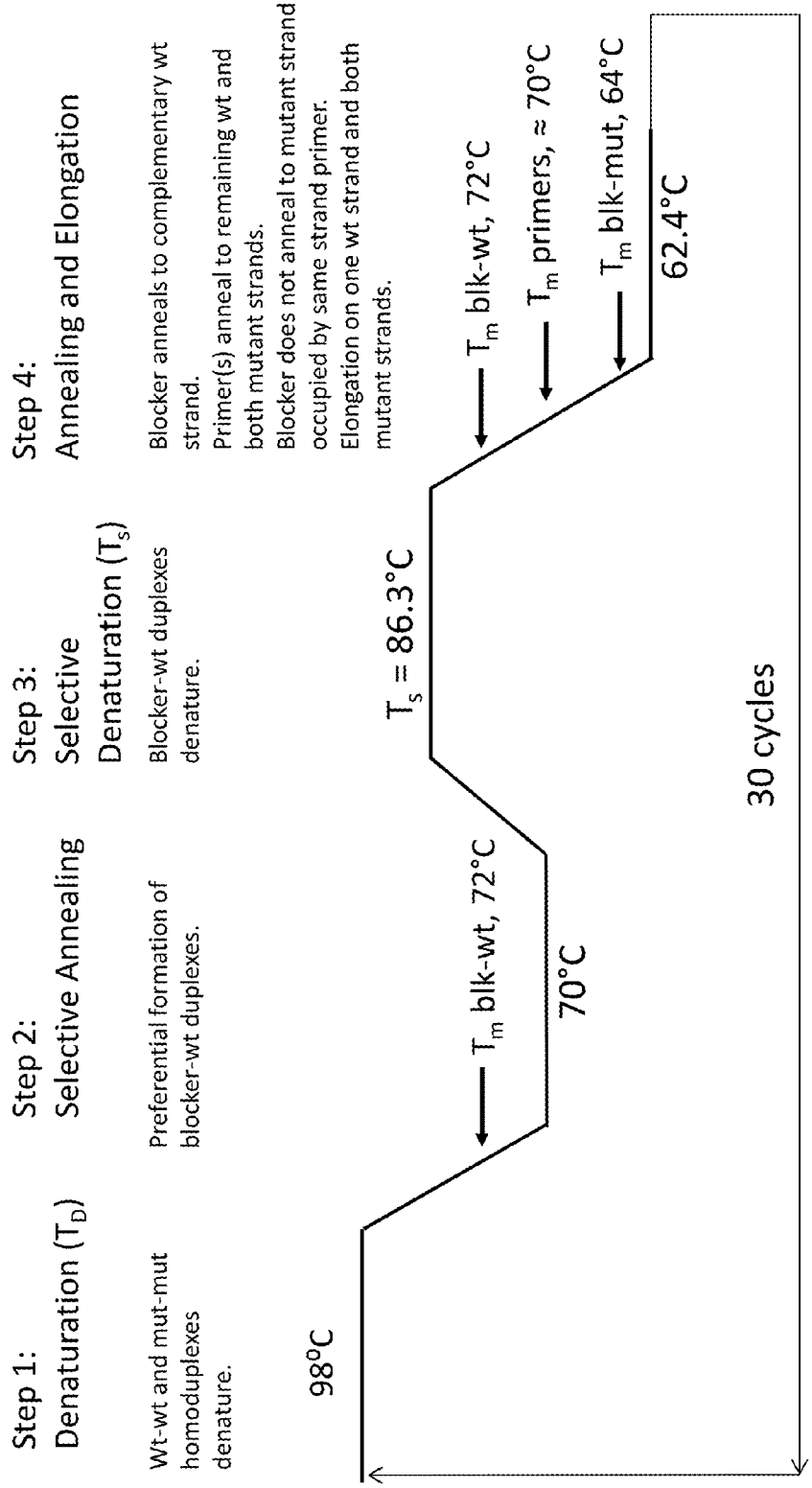
FIG. 2 illustrates one embodiment of the present method.

A schematic example of a four-step PCR enrichment assay (EGFR Exon 20 T790M) is provided in FIG. 2. In this assay, a 98° C. denaturation step ensures that all duplexes denature. During the second (optional) step (70° C.) blocker-wildtype duplexes form, but few blocker-mutant duplexes form (as 70° C. is above the blocker-mutant Tm). At step 3, selective denaturation, many of the blocker-wildtype will denature (along with any blocker-mutant duplexes that may exist). Just as in the two-step PCR (example 1), as the reaction ramps back to the annealing temperature of 64.0° C., complementary wildtype strands are bound by the excess blocker before the primers anneal. The primers then anneal to the complementary mutant strand and bar the possibility of blocker binding to that mutant strand. Short amplicon length allows extension without the need for an additional elongation step.

The level of enrichment for EGFR T790M_T is provided below in Table 6

TABLE 6

| Input | FOLD ENRICHMENT EGFR T790M_T |
|---|---|
| 5 | 4714 |
| 50 | 1691 |
| 100 | 980 |

Example 3

Figure 3:
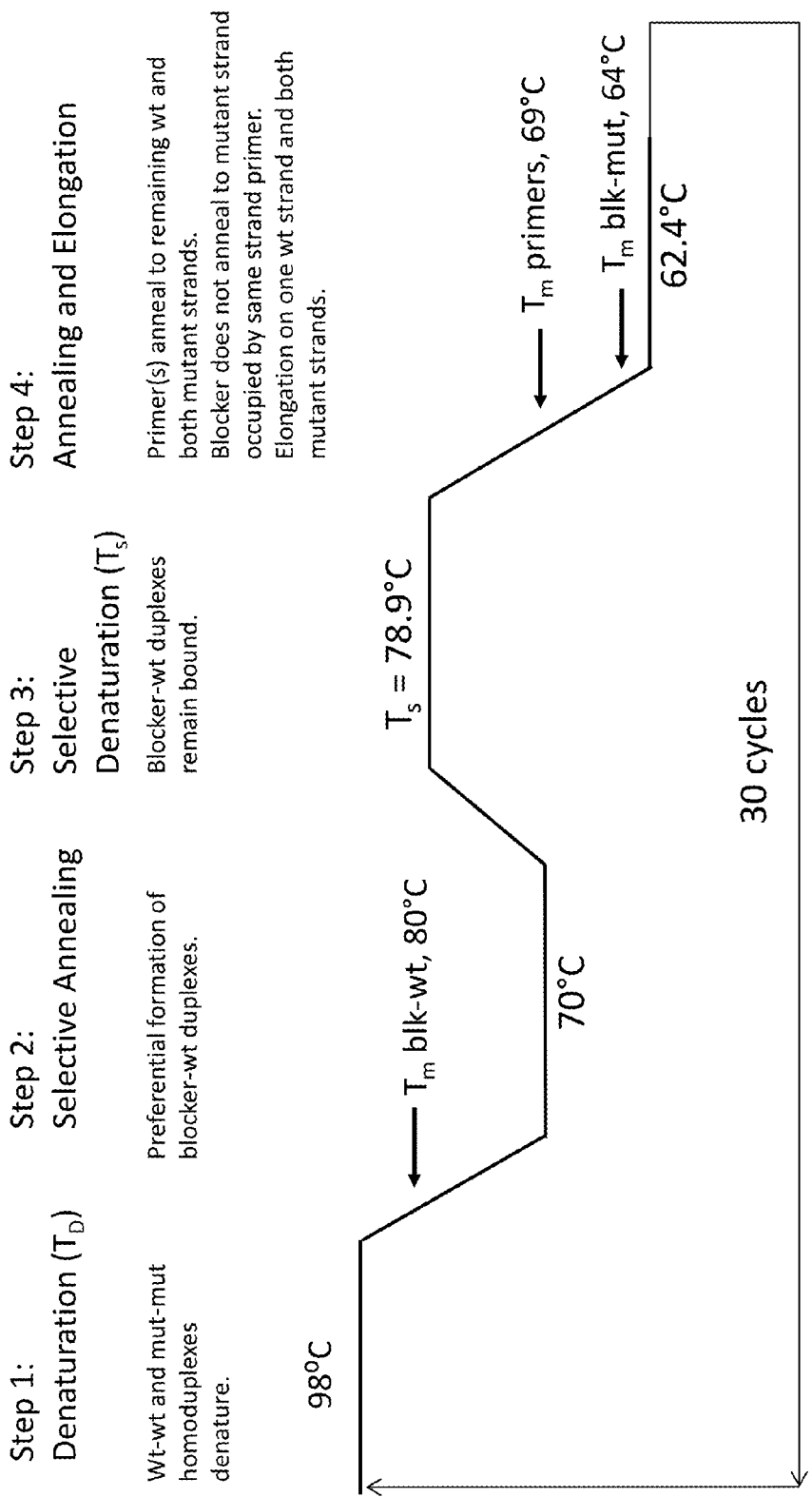
FIG. 3 illustrates one embodiment of the present method.

FIG. 3 provides an example of a four-step PCR enrichment assay for KRAS Exon 2 single-base substitution. This assay proceeds in a similar fashion as Example 2 except that the selective denaturation step is chosen below the wildtype-blocker Tm. The temperature differential between the blocker-wildtype Tm, the primer-template Tm and the blocker-mutant Tm is much greater than in example 2, leading to a more efficient enrichment.

The above Examples demonstrate application of the kinetics-based design of primer and blocker sequences (based on the relationship between various reaction components) for substantial enrichment of low-abundance target sequence in a background of reference nucleic acid.

Example 4

Kinetic Based Design of Blocker and Primer Sequences

Figure 4:
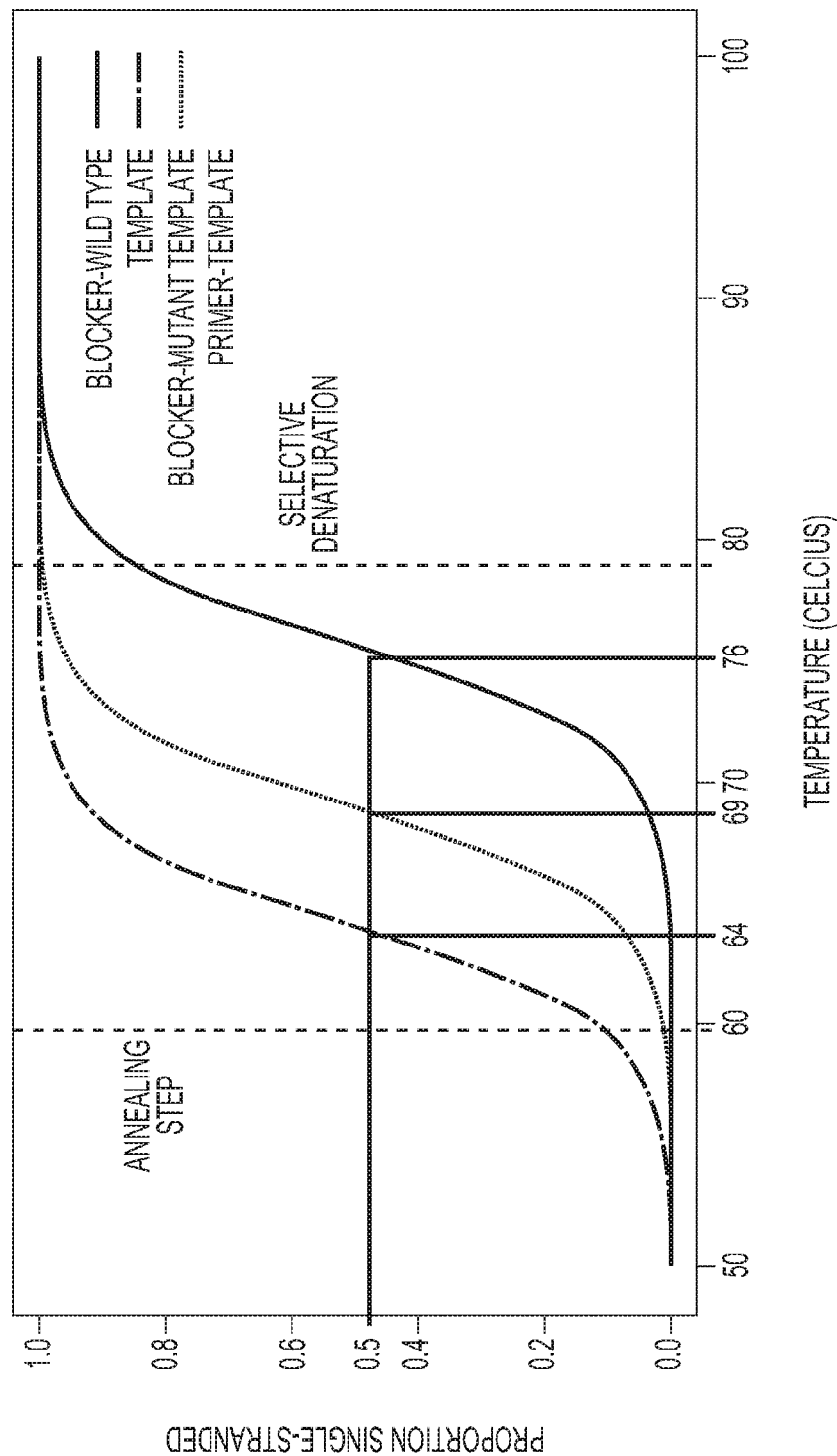
FIG. 4 illustrates melting temperature profiles.

FIG. 4 provides a schematic which diagrams and illustrates simplified melting temperature profiles for the blocker-wildtype template (Tm=80° C.), blocker-mutant template (Tm=64° C.), and primer-template duplexes (Tm=69° C.). The given curves are illustrated using the KRAS assay—but the principle is general. Each oligonucleotide has an approximately sigmoid (logistic) melting temperature profile with an oligonucleotide's Tm (under assay conditions) being the temperature at which 50% of the molecules are on average single-stranded, and 50% are bound to their template as a double-stranded formation. The process is dynamic in that individual molecules continually melt and re-anneal at this temperature. It can be seen that at the selective denaturation temperature nearly 100% of the primer and the blocker-mutant template duplexes are dissociated whereas around 18% of the blocker-wild type duplex may remain intact. Conversely, by the time the temperature ramps down to the primer Tm of 69° C. almost all of the wildtype molecules will have bound the blocker whereas nearly all mutant molecules will remain single stranded. Since there is overlap in sequence between the blocker and the primer that binds with the same sense as the blocker, the primer will largely be prevented from binding to wildtype. Similarly, by the time the temperature ramps down to the blocker-mutant template Tm of 64° C., nearly all mutant sequence will have bound to the primer and relatively little blocker is therefore able to bind to the mutant even though the "annealing" temperature of 60° C. is below the blocker-mutant template Tm. These curves are simplistic because they represent "equilibrium" conditions at each temperature. The kinetics of melting and annealing may take a short period of time (to a few seconds) to reach equilibrium and therefore the temperature profiles will in reality exhibit some lag.

Applying kinetic considerations, preferred melting temperature of preselected primer is designed so as to include:
a) lower than the melting temperature of blocker-wt product;
b) higher than the melting temperature of the blocker-mutant product;
c) blocker can overlap with one primer or two primers;
d) blocker need not have overlap with a primers; and/or
d) an empirically derived selective denaturation (Tsd) can be higher (e.g., EGFRdel and EGFR T790) or lower (e.g., KRAS) than the melting temperature of a blocker-wt product but generally will be higher than the temperature allowing annealing of the primer to a fully complementary sequence.

Figure 5:
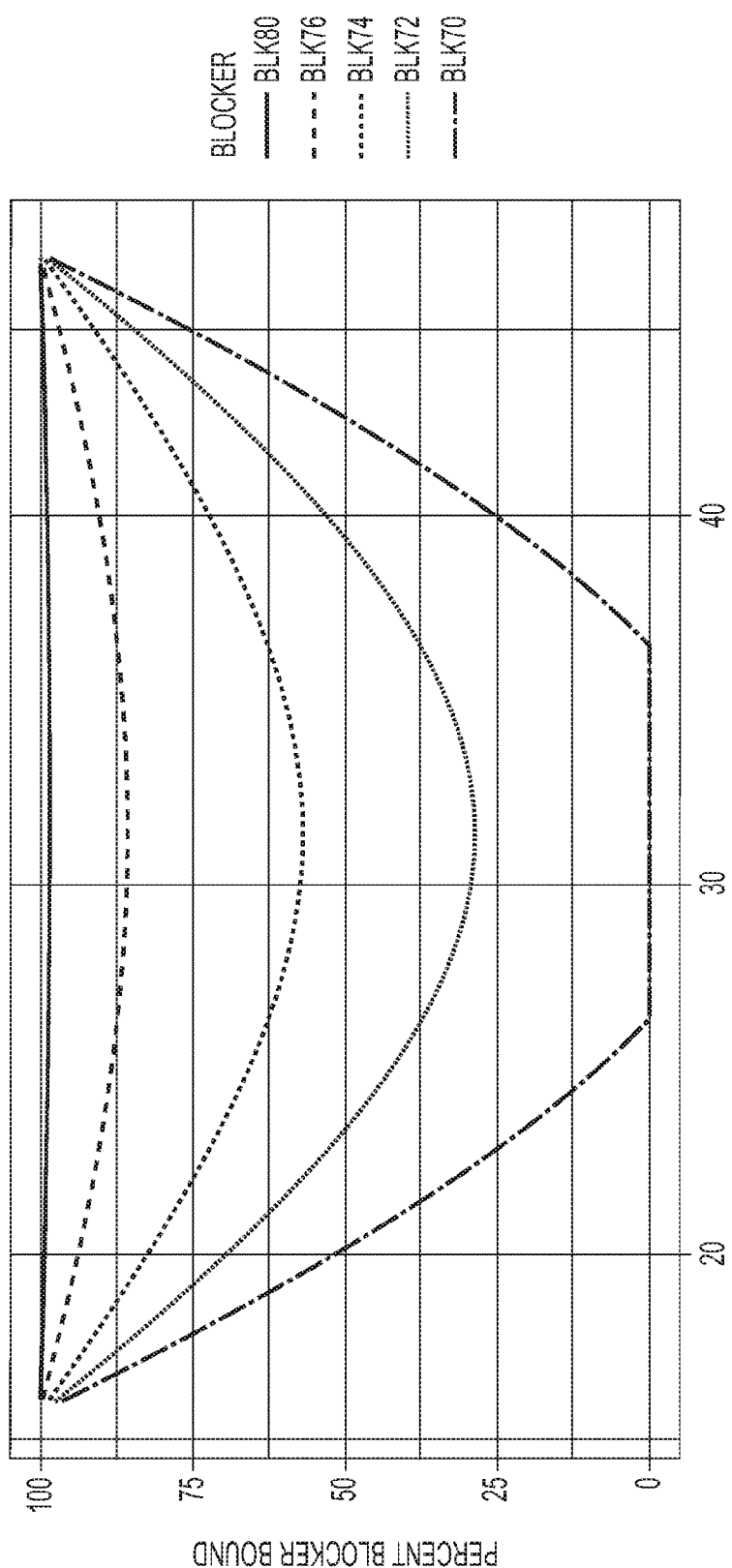
FIG. 5 illustrates an exemplary kinetics profile of different blocker.

FIG. 5 provides a diagram illustrating how the percentage of a blocker that is bound to a target sequence (e.g., a wildtype blocker with a Tm of 76° C.) changes over time as the temperature of the reaction approaches a selective denaturation temperature of 78.9° C.

Example 5

Verification of a Single Copy Assay Sensitivity

Figure 6:
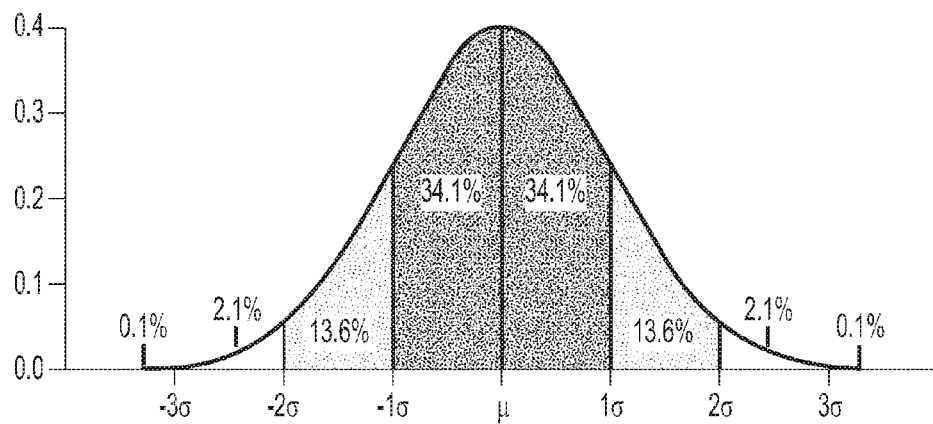
FIG. 6 illustrates Poisson distribution utilized to verify single copy assay sensitivity.

FIG. 6 provides a Normal distribution histogram and Poisson probabilities table. The table on the right is a Poisson distribution table of probabilities. The columns of the table are the number of observed events in a discrete interval. The rows are the average number of events per interval (0.13 events per interval, 0.25 events per interval, etc.) Each cell in the table is the probability of observing a given number of events (columns) given an average expected number of events (rows) in a single interval. For example, with regards to a cancer mutation detection test, if we expect to detect 2 mutants DNA strands per milliliter (interval), a single milliliter would have a 14% chance of containing no mutant DNA strands at all.

Figure 7:
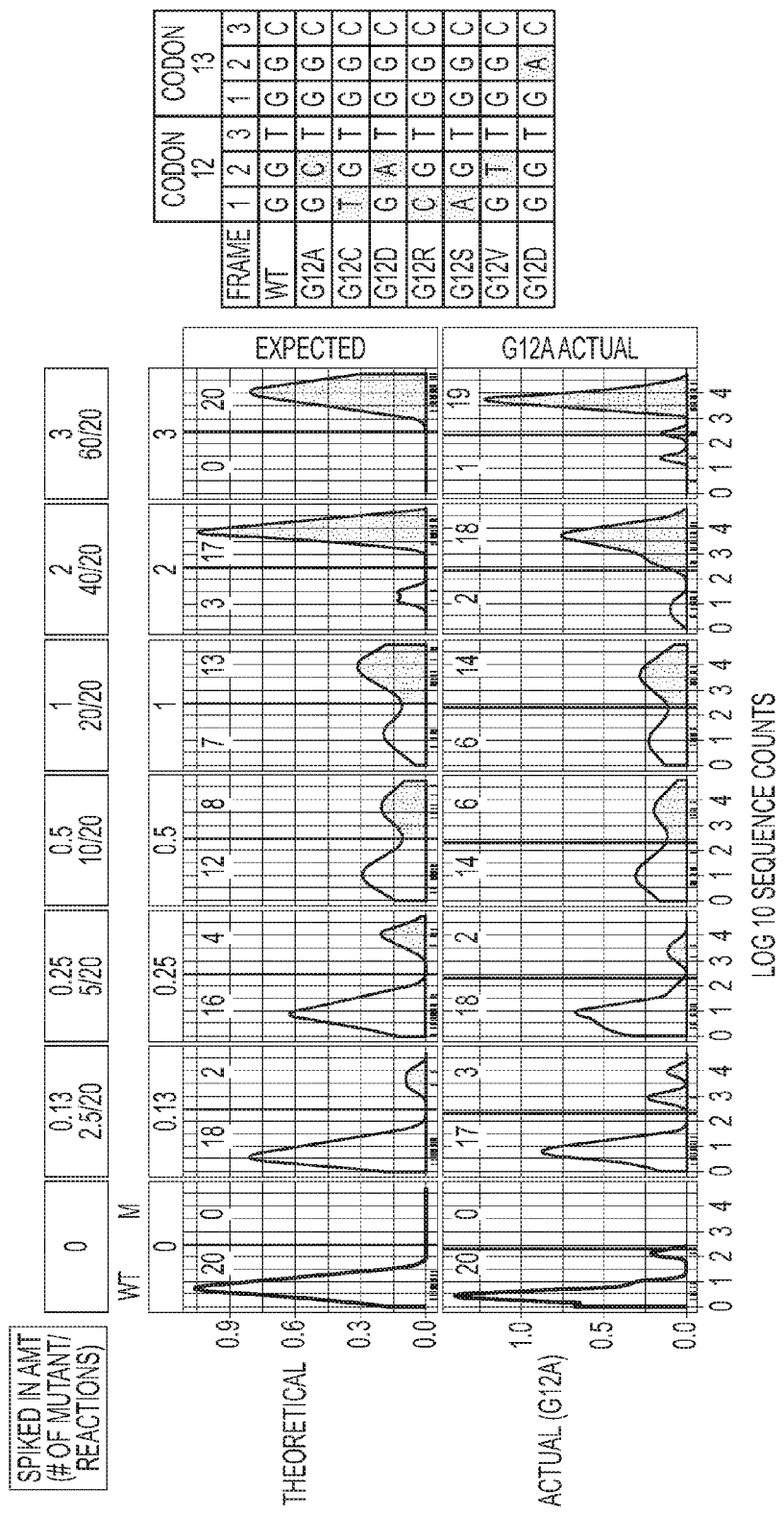
FIG. 7 illustrates demonstration of single copy sensitivity of KRAS assay.

FIG. 7 Curve fit and calculated input mutation level of a cancer patient was detected in a biological fluid sample from the patient containing the KRAS G12D mutation. The raw data plot of the enriched reference data shows a best fit to a hyperbolic curve (also known as a saturation binding or dose response curve) demonstrating a strong non-linear enrichment of low level mutant species. Mutant DNA input at 0.2%, 0.05%, 0.01% and 0.0% of the total DNA returned observed detection levels of 18.25%, 4.45%, 1.84% and 0.54% respectively as a percentage of the total sequence reads.

Example 6

Single Copy Sensitivity of KRAS Assay

FIG. 7 demonstrates an example of theoretical and experimental distribution results of an assay verifying single copy sensitivity of a target KRAS G12A. On the left is divided into 14 sub plot depicting distributions. The top row of distributions depict a theoretical expectation for 20 measurements given the average copy spiked-in input labeled above each distribution. The bottom row depicts actual experimental results. The x-axis of each subplot is the number of mutant sequence reads (log scale) detected by the assay. The y-axis of each subplot is a density measure of the data points along the x-axis, the closer the points are together, the higher the density. The area under the density curve is one. The bimodal distribution of points, represented by the density curve, provides an intuitive cutpoint (blue line) between detected (MT) and not detected (WT) samples. The numerals in each subplot indicate the number of samples (of 20) which were detected (right side of cutpoint) and not detected (left side of cutpoint).

Example 7

Detection of KRAS Mutations in a High Background of Wildtype DNA Sequence

Figure 8:
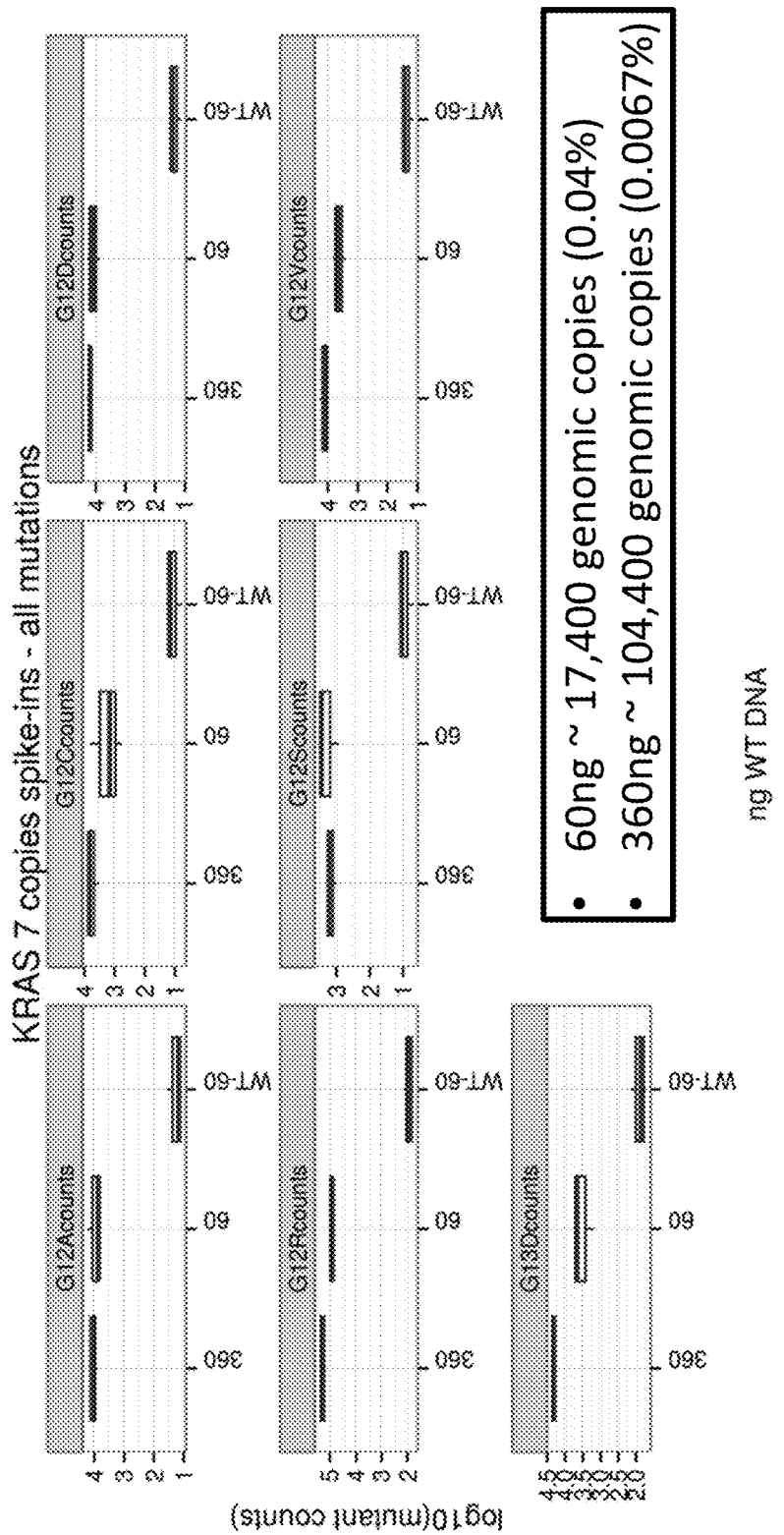
FIG. 8 illustrates substantial enrichment of a low-abundance target sequence.

FIG. 8 provides results of an assay wherein mutant was detected at background levels of starting 60 ng and 360 ng total nucleic acid in the sample used for reaction. Detection of 7 mutant copies in a background of either 60 ng (17,400 copies) wildtype genomic DNA or 360 ng (104,400 copies) wildtype genomic DNA. The figure s is divided into 7 subplots, each depicting the results for one of the seven KRAS mutations detected by the assay (G12A,G12C,G12D, G12R,G12S,G12V,G13D). The x-axis of each subplot lists the three sample types tested: 7 mutant copies in 17,400 wildtype background, 7 mutant copies in 104,400 wildtype DNA background, and wildtype only (17,400 copies). The y-axis of each subplot is the number of mutant sequence reads (log scale) detected by the assay.

Example 8

Integration of Enrichment PCR with Mutation Detection by Droplet Digital PCR

Figure 9:
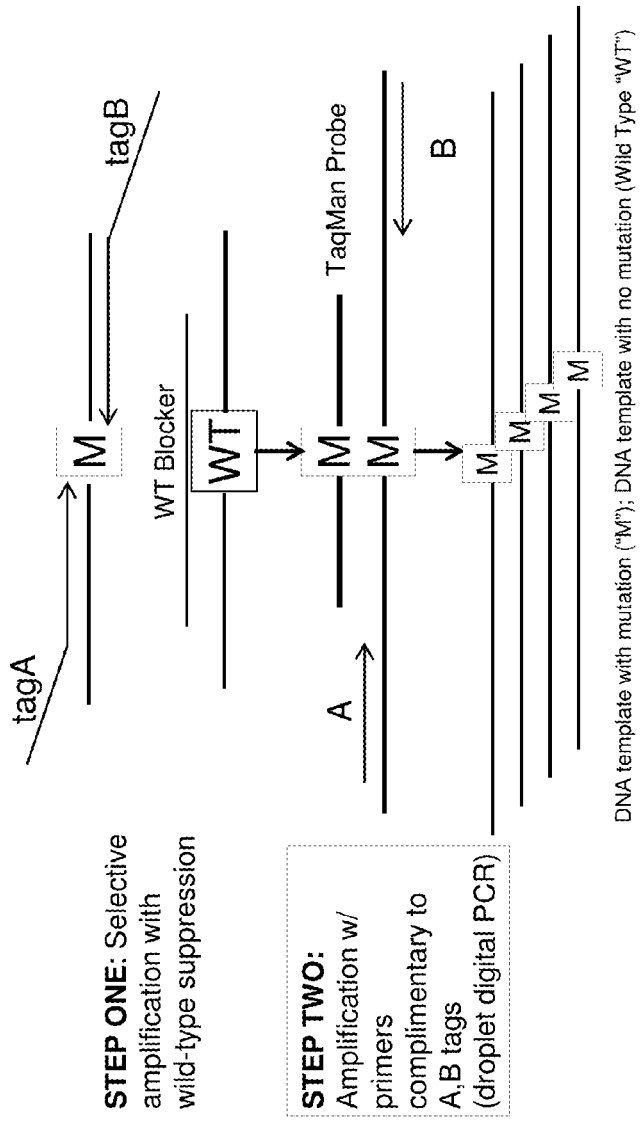
FIG. 9 provides a schematic of one embodiment of the present method.

FIG. 9 shows BRAF V600E mutation detection assay design for integration with droplet digital PCR (RainDance, Billerica, Mass.). The first step involved pre-amplification with two primers flanking the BRAF V600E locus, where both primers contain non-complementary 5' tags which hybridize to second round primers. A complementary blocking oligonucleotide suppressed wt BRAF amplification, achieving enrichment of the mutant BRAF V600E sequence within the pre-amplification step. The second step entailed a duplex ddPCR reaction using FAM (V600E BRAF) and VIC (wt BRAF) TaqMan probes to enable differentiation of mutant versus wild-type quantification, respectively. The RainDrop ddPCR instrument (RainDance; Billerica, Mass.) was used for PCR droplet separation, fluorescent reading, and counting droplets containing mutant sequence, wt sequence, or unreacted probe.

Example 9

Integration with Next Generation Sequencing

Figure 10:
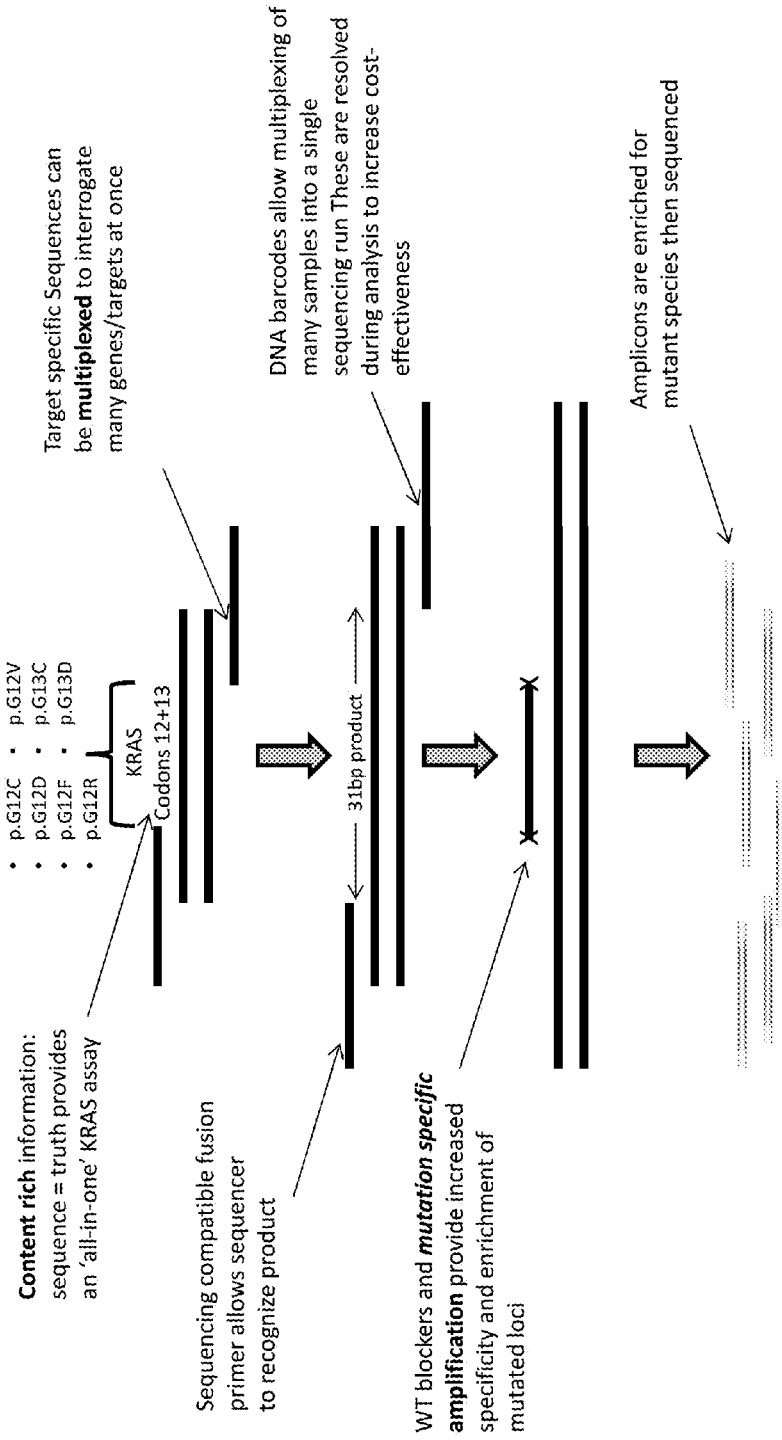
FIG. 10 provides a schematic of one embodiment of the present method.

Use of the method in conjunction with further target sequence detection by next generation sequencing method is provided in FIG. 10.

FIG. 10—Designed of an ultra-short assay to detect the KRAS gene mutations in codons 12 and 13. Assay utilizes a 31 bp footprint, contains a pre-amplification step that specifically enriches mutated DNA fragments and detects at least 7 different KRAS mutations in Exon 2 region. Wiletype sequence blocker and mutation specific amplification provide increased specificity and enrichment of mutated loci.

Example 10

Figure 11:
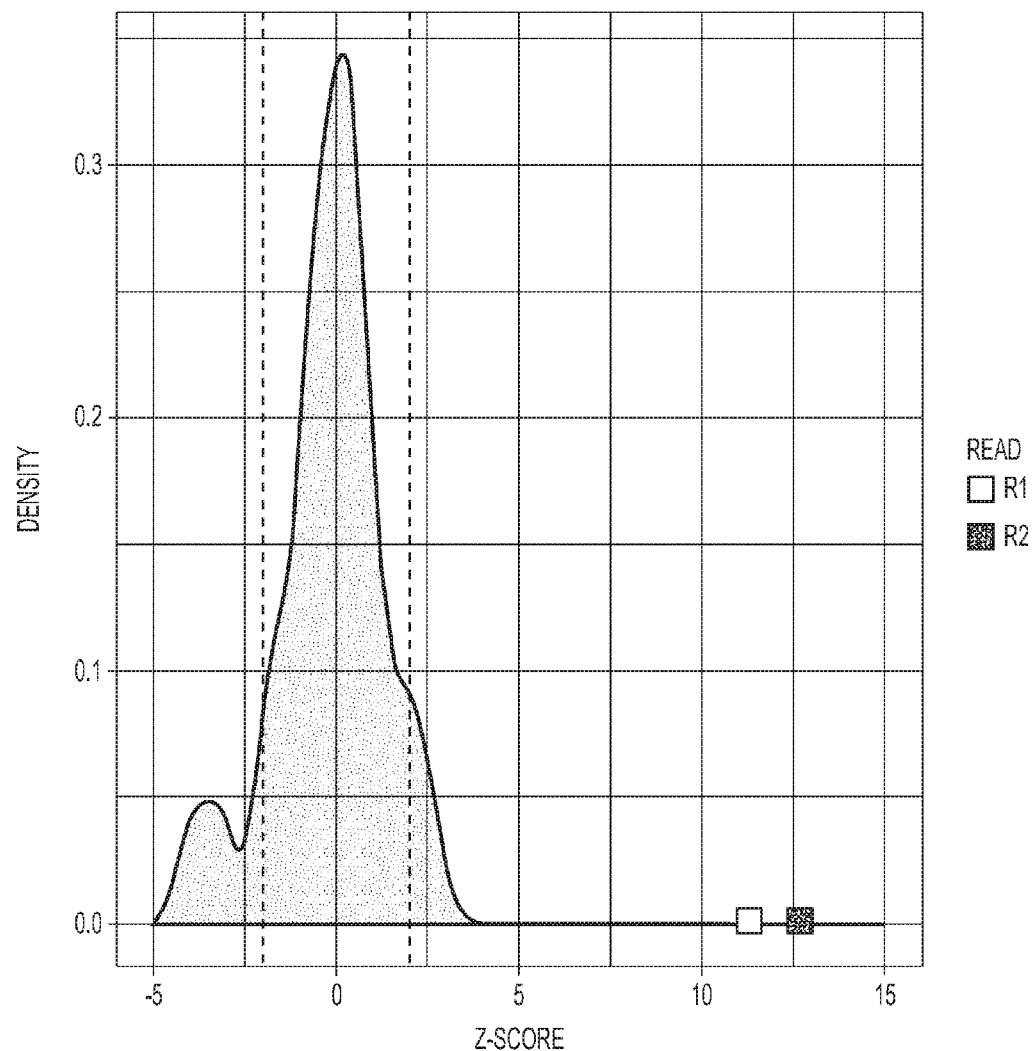
FIG. 11 illustrates one embodiment of the present method.

FIG. 11—Establishing detection cutoffs using MAD scores. Dotted vertical lines represent z-score cutoffs of 2 sigma. z score density distribution of KRAS G12V target/non-target ratios observed in a healthy control (grey) with mutation detection results from colon cancer patient (h.), forward reads (gold point) and reverse reads in (blue point).

Figure 12:
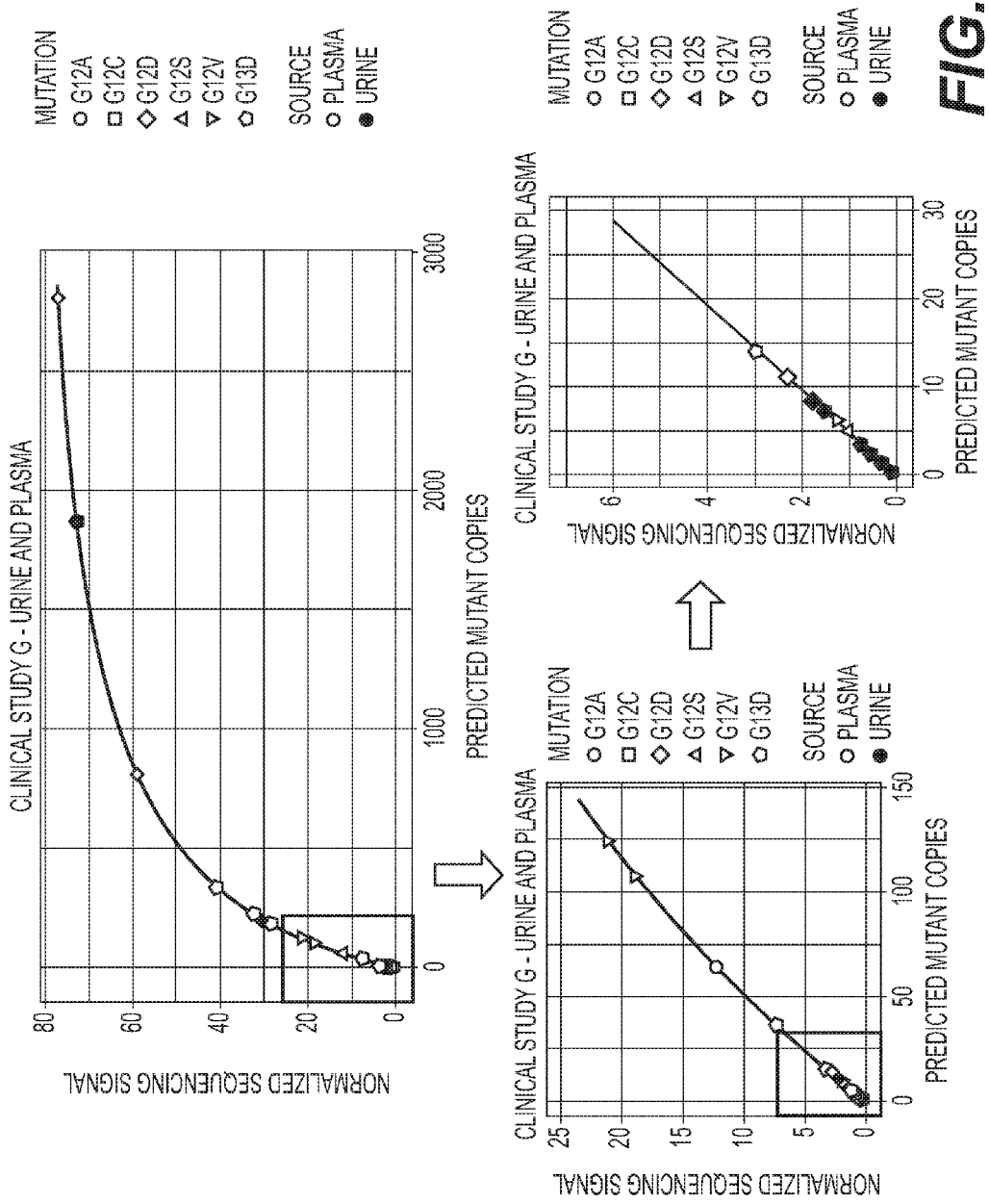
FIG. 12 illustrates clinical application of one embodiment of the present method.

FIG. 12 provides results of an assay of the method allowing quantitating input copy number: Standard curves were generated for each mutation at levels varying from 5 to 500 input mutant copies. Both the unknown samples and standard samples were enriched with the same method. Follow sequencing mutant read counts above a cutoff value were plotted onto their respective standard curve to calculate the input copy number. Unknown samples copy number input was calculated based on plotting to the standard curve for the mutation of interest. From left to right figures show the same data scaled up to 3000 mutations on the left and 30 mutations on the right demonstrating excellent linearity at lower level inputs. As the mutant copy drops the curve linearizes and tightens to provide better quantitation at low mutational load.

Example 11

Detection of KRAS G12S in a Cancer Patient

Figure 13:
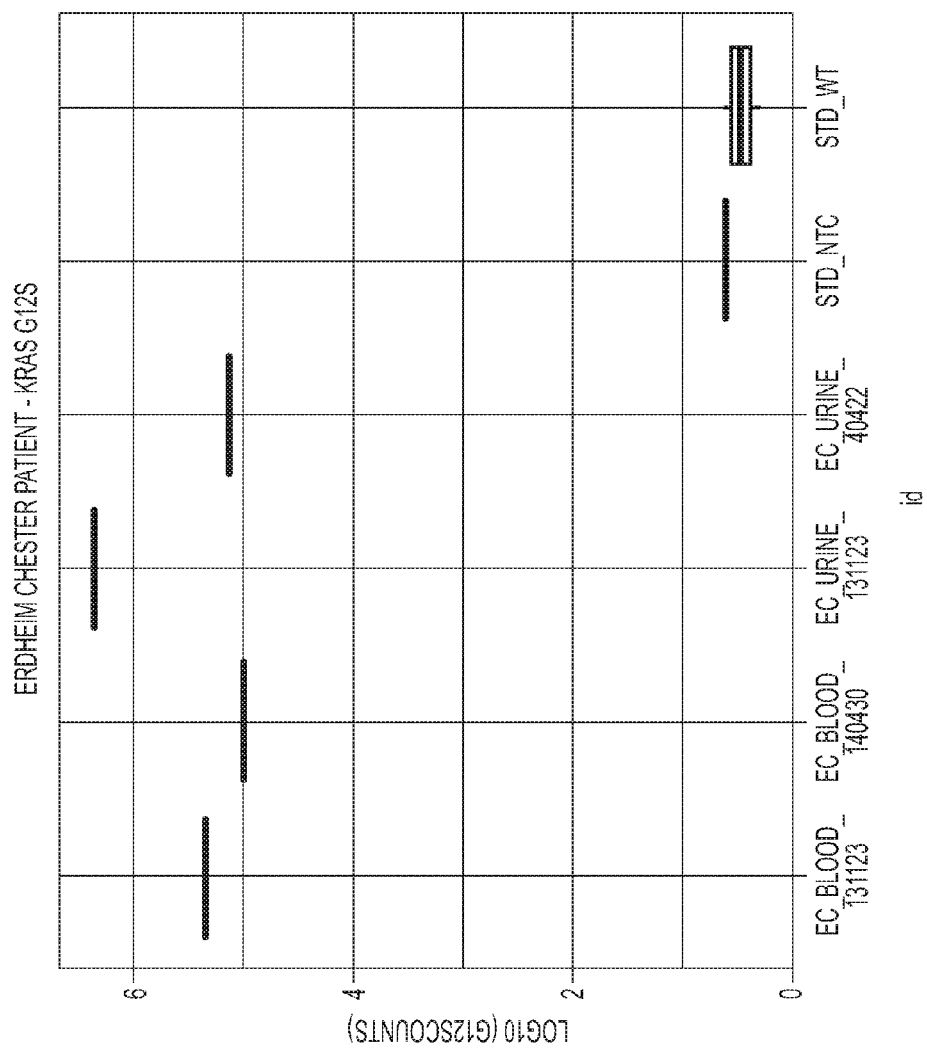
FIG. 13 illustrates clinical application of one embodiment of the present method.

FIG. 13 depicts detection of KRAS G12S mutant DNA in fluid samples from an Erdheim Chester Patient cancer patient. Urine and blood were collected from a single Erdheim Chester patient at several time points: Nov. 13, 2013 (urine and blood), Apr. 22, 2014 (urine) and Apr. 30, 2014 (blood). The KRAS assay was run on DNA extracted from all samples in the same run with 20 wildtype standard control (STD_WT) and 3 no-template control (STD_NTC). The y-axis is the number of mutant sequence reads (log scale) detected by the assay.

Example 12

Application of the method for designing blocker and primer sequences having preselected melting temperature are provided below with exemplary target specific primers presented in Table 7, exemplary blocker sequences presented in Table 8, target specific primers for EGFR 858 target sequence presented in Table 9, and primer sequence for EGFR T790M presented in Table 10 below.

TABLE 7

| | | Tag Sequence | Target-Specific Sequence (Forward) | Oligonucleotide Sequence | Tag Name | Target Name | Oligo Name |
|---|---|---|---|---|---|---|---|
| | | | TARGET SPECIFIC PRIMERS | | | | |
| | | | Forward Primers | | | | |
| 1 | | ACACTGACGA-CATGGTTCTACA (SEQ ID NO: 1) | ACTGTCCAGCT-TTGTGCC (SEQ ID NO: 2) | ACACTGACGACA-TGGTTCTACAACT-GTCCAGCTTTGTGCC (SEQ ID NO: 3) | CS1 | TP53 | CS1-TP53-1-for |
| 2 | | ACACTGACGA-CATGGTTCTAC-A (SEQ ID NO: 1) | GATCATCATAG-GAGTTGCATTG-TTG (SEQ ID NO: 4) | ACACTGACGACA-TGGTTCTACAGAT-CATCATAGGAGT-TGCATTGTTG (SEQ ID NO: 5) | CS1 | TP53 | CS1-TP53-2-for |
| | | | Reverse Primer | | | | |
| 1 | | TACGGTAGCA-GAGACTTGGT-CT (SEQ ID NO: 6) | TCCTCTGCCTA-GGCGTT (SEQ ID NO: 7) | TACGGTAGCAGA-GACTTGGTCTTCC-TCTGCCTAGGCGT-T (SEQ ID NO: 8) | CS2 | TP53 | CS2-TP53-1-rev |
| 2 | | TACGGTAGCA-GAGACTTGGT-CT (SEQ ID NO: 6) | GAAATGTAAAT-GTGGAGCCAA-ACA (SEQ ID NO: 9) | TACGGTAGCAGA-GACTTGGTCTGA-AATGTAAATGTG-GAGCCAAACA (SEQ ID NO: 10) | CS2 | TP53 | CS2-TP53-2-rev |

TABLE 8

| Blocker Name | Sequence | Exiqon Tm |
|---|---|---|
| BLOCKER SEQUENCES | | |
| EGFRdel Blocker1 | C3-CGGCCTCTTCATGC-C3 (SEQ ID NO: 11) | 68 C. |
| EGFRdel Blocker2 | C3-CGGCCTCTTCATGC-PO4 (SEQ ID NO: 12) | 72 C. |
| EGFR L858 Blocker1 | C3-GATTTTGGGCTGGCC-C3 (SEQ ID NO: 13) | 69 C. |
| EGFR L858 Blocker2 | C3-TTTTGGGCTGGCCA-C3 (SEQ ID NO: 14) | 71 C. |
| EGFR T790 Blocker1 | C3-GCAGCTCATCACGC-C3 (SEQ ID NO: 15) | 70 C. |
| PIK3CA 545-6 Blocker1 | C3-AATCACTGAGCAGGA-C3 (SEQ ID NO: 16) | 68 C. |
| PIK3CA 1047 Blocker1 | C3-CCAGCCACCATGAT-C3 (SEQ ID NO: 17) | 69 C. |
| EGFR L858 Blocker3 | C3-GATTTTGGGCTGGCCAA-C3 (SEQ ID NO: 18) | 72 C. |

| Name | Oligo | Sequence | | |
|---|---|---|---|---|
| OTHER (FL1 FL2) | | | | |
| FL1 | CS1 | ACACTGACGACATGGTT CTACA (SEQ ID NO: 19) | 69 C. | |
| | C52 | TACGGTAGCAGAGACTT GGTCT (SEQ ID NO: 20) | 71 C. | |
| FL2 | CS1rc | TGTAGAACCATGTCGTC AGTGT (SEQ ID NO: 21) | 69 C. | |
| | CS2rc | AGACCAAGTCTCTGCTA CCGTA (SEQ ID NO: 22) | 71 C. | |
| HBV 1762 | | | | |
| HBV 1762 WT blk1 | | AGGTTAAAGGTCT (SEQ ID NO: 23) | 65 | A{G}GT{THA}{A}{A}G{G}T{C}T (SEQ ID NO: 23) |
| HBV 1762 WT blk2 | | AGGTTAAAGGTCT (SEQ ID NO: 23) | 65 | AG{G}{T}{T}{A}A{A}G{G}{T}CT (SEQ ID NO: 23) |
| HBV 1762 WT blk3 | | ACAAAGACCTTTAACC (SEQ ID NO: 24) | 68 | A{C}{A}{A}A{G}A{C}{C}{T}TTAACC (SEQ ID NO: 24) |
| HBV 1762 WT blk4 | | GTACAAAGACCTTTAAC C (SEQ ID NO: 25) | 68 | G{T}A{C}A{A}A{G}A{C}{C}{T}TTAACC (SEQ ID NO: 25) |
| HBV 1762 WT blk5 | | GTACAAAGACCTTTAAC (SEQ ID NO: 26) | 68 | G{T}A{C}AA{A}{G}A{C}{C}{T}T{T}AAC (SEQ ID NO: 26) |
| HBV 1762 WT blk5 | Metabion (MB) | ZNA4-A(pdC)AAAGA(pdC)(pdC)TTTAA(pdC)(pdC)-PO4 (SEQ ID NO: 27) | 69.4 | No 5' spacer; 3' phosphate |
| EGFR T790M | | | | /5SpC3/CATCACGCAGCTC/3SpC3/ (SEQ ID NO: 28) |
| EGFR T790M WT blk1 | | CATCACGCAGCTC (SEQ ID NO: 29) | 70 | indicates LNAs, underline indicates the T790M mutation |
| EGFR T790M WT blk2 | | TCATCACGCAGCT (SEQ ID NO: 30) | 69 | |
| EGFR T790M WT blk3 | | TCATCACGCAGC (SEQ ID NO: 31) | 69 | |
| EGFR T790M WT blk4 | | AGCTGCGTGATG (SEQ ID NO: 32) | 69 | |
| EGFR T790M WT blk5 | | CTGCGTGATGAG (SEQ ID NO: 33) | 70 | |

TABLE 8-continued

BLOCKER SEQUENCES

| | | | |
|---|---|---|---|
| EGFR T790M WT blk6 | CTCATCACGCAGCT (SEQ ID NO: 34) | 80 | /5SpC3/CTCATCACGCAGCT/ 3SpC3/ (SEQ ID NO: 35) |
| EGFR T790M WT blk7 | CTCATCACGCAGCTC (SEQ ID NO: 36) | 79 | /5SpC3/CTCATCACGCAGCTC/ 3SpC3/ (SEQ ID NO: 37) |
| EGFR T790M WT blk8 | GAGCTGCGTGATGAG (SEQ ID NO: 38) | 81 | /5SpC3/GAGCTGCGTGATGAG/ 3SpC3/ (SEQ ID NO: 39) |
| EGFR T790M WT blk9 | GAGCTGCGTGATGA (SEQ ID NO: 40) | 81 | /5SpC3/GAGCTGCGTGATGA/ 3SpC3/ (SEQ ID NO: 41) |
| EGFR T790M RS WT bk10 | GCATGAGCTGCgTGATG (SEQ ID NO: 42) | 85 | /5SpC3/GCATGAGCTGCgTGATG/ 3SpC3/ (SEQ ID NO: 43) |
| EGFR T790M FS WT bk11 | GCTCATCACGCAGCTC (SEQ ID NO: 44) | 87 | /5SpC3/GCTCATCACGCAGCTC/ 3SpC3/ (SEQ ID NO: 45) |
| EGFR T790M FS WT bk12 | GTGCAGCTCATCACGCA GCTC (SEQ ID NO: 46) | 87 | /5SpC3/GTGCAGCTCATCAC GCAGCTC/3SpC3/ (SEQ ID NO: 47) |
| BRAF WT F blk 5 | GGTCTAGCTACAGTGAA A (SEQ ID NO: 48) | 79 | /5SpC3/GGTCTAGCTACAG TGAAA/3SpC3/ (SEQ ID NO: 49) |
| BRAF WT R blk 7 | CCATCGAGATTTCACTG T (SEQ ID NO: 50) | 81 | /5SpC3/CCATCGAGATTTC ACTGT/3SpC3/ (SEQ ID NO: 51) |
| EGFR L858 Blocker4 | TTTTGGGCTGGCC (SEQ ID NO: 52) | 77 | /5SpC3/TTTTGGGCTGGCC/3 SpC3/ (SEQ ID NO: 53) |
| EGFR L858 Blocker5 | TTTTGGGCTGGCCA (SEQ ID NO: 54) | 79 | /5SpC3/TTTTGGGCTGGCCA/ 3SpC3/ (SEQ ID NO: 14) |
| EGFR L858 Blocker6 (rc) | AGTTTGGCCAGCC (SEQ ID NO: 55) | 77 | /5SpC3/AGTTTGGCCAGCC/ 3SpC3/ (SEQ ID NO: 56) |
| EGFR L858 Blocker7 (rc) | CAGTTTGGCCAGCCCA (SEQ ID NO: 57) | 79 | /5SpC3/CAGTTTGGCCAGCCCA/ 3SpC3/ (SEQ ID NO: 58) |
| KRAS-Q61- BLK1 | ctcCTCttgacctg (SEQ ID NO: 59) | 77 | /5SpC3/ctcCTCttgacctg/ 3SpC3/ (SEQ ID NO: 60) | all w/ C3 spacer on 5' and 3' ends unless indicated

TABLE 9

EGFR 858

| Primer | Oligo Name | Oligonucleotide Sequence | SEQ ID NO: |
|---|---|---|---|
| FP1 | CS1-EGFR L858-6-for | ACACTGACGACATGGTTCTACACACAGATTTTGGGC | 61 |
| FP2 | CS1-EGFR L858 FP2-12-for | ACACTGACGACATGGTTCTACACACAGATTTTGGGC | 61 |
| FP3 | CS1-EGFR L858 FP3-13-for | ACACTGACGACATGGTTCTACATCACAGATTTTGGGC | 62 |
| FP4 | CS1-EGFR-L858R-FP4-55-for | ACACTGACGACATGGTTCTACAGATCACAGATTTTGGGC | 63 |
| FP5 | CS1-EGFR-L858R-FP5-56-for | ACACTGACGACATGGTTCTACAAGATCACAGATTTTGGG | 64 |
| FP6 | CS1-EGFR-L858R-FP6-57-for | ACACTGACGACATGGTTCTACAAGATCACAGATTTTGG | 65 |
| FP6b | EGFR-L858-FP6-81-F | ACACTGACGACATGGTTCTACAAGATCACAGATTTTG | 66 |
| FP7 | EGFR-L858-FP7-82-F | ACACTGACGACATGGTTCTACAAGATCACAGATTTTGG | 67 |
| FP8 | EGFR-L858-FP8-83-F | ACACTGACGACATGGTTCTACAGTCAAGATCACAGATTTT | 68 |
| FP9 | CS1-EGFR-L858R-FP9-84-for | ACACTGACGACATGGTTCTACAGTCAAGATCACAGATTTT | 68 |

TABLE 9 -continued

EGFR 858

| Primer | Oligo Name | Oligonucleotide Sequence | SEQ ID NO: |
|---|---|---|---|
| FP10 | CS1-EGFR-L858R-FP10-85-for | ACACTGACGACATGGTTCTACATCAAGATCACAGATTTT | 69 |
| RP1 | EGFR-L858 | TACGGTAGCAGAGACTTGGTCTCGCACCCAGCAGTT | 70 |
| RP2 | EGFR L858 RP2 | TACGGTAGCAGAGACTTGGTCTCGCACCCAGCAGT | 71 |
| RP3 | EGFR L858 RP3 | TACGGTAGCAGAGACTTGGTCTGCACCCAGCAGTT | 72 |
| RP4 | EGFR L858 RP4 | TACGGTAGCAGAGACTTGGTCTCGCACCCAGCAGT | 71 |
| RP5 | EGFR-L858R-RP7 | TACGGTAGCAGAGACTTGGTCTCCGCACCCAGCAG | 73 |
| RP6 | EGFR-L858R-RP8 | TACGGTAGCAGAGACTTGGTCTTTCCGCACCCAGC | 74 |
| Blk1 | EGFR L858 Blocker1 | C3-GATTTTGGGCTGGCC-C3 | 13 |
| Blk2 | EGFR L858 Blocker2 | C3-TTTTGGGCTGGCCA-C3 | 14 |
| Blk3 | EGFR L858 Blocker3 | C3-GATTTTGGGCTGGCCAA-C3 | 18 |
| Blk4 | EGFR L858 Blocker4 | /5SpC3/1TTTGGGCTGGCC/3SpC3/ | 53 |
| Blk5 | EGFR L858 Blocker5 | /5SpC3/1TTTGGGCTGGCCA/3SpC3/ | 14 |
| Blk6 | EGFR L858 Blocker6 (rc) | /5SpC3/AGTTTGGCCAGCC/3SpC3/ | 56 |
| Blk7 | EGFR L858 Blocker7 (rc) | /5SpC3/CAGTTTGGCCAGCCCA/3SpC3/ | 58 |
| Blk8 | EGFR-L858-Blk8-rc | /5SpC3/AGTTTGGCcAGCCCA/3SpC3/ | 75 |
| Blk9 | EGFR-L858-Blk9-rc | /5SpC3/AGTTTGGCCaGCCCA/3SpC3/ | 75 |
| Blk10 | EGFR-L858-Blk10 | /5SpC3/CAGTTTGGCcaGCCC/3SpC3/ | 76 |
| Blk11 | EGFR-L858-Blk11 | /5SpC3/1TTGGGCtGGCCAAA/3SpC3/ | 77 |
| Blk12 | EGFR-L858-Blk12 | /5SpC3/ATTTTGGGCtGGCCA/3SpC3/ | 78 |
| Blk13 | EGFR-L858-Blk13 | /5SpC3/GATTTTGGGCtGGCCA/3SpC3/ | 79 |

TABLE 10

EGFR T790M rs121434569 [Homo sapiens]
tctgcctcacctCCACCGTGCAGCTCATCA[C/T]GCAGCTCATGCCC
Ttcggctgcctcctgga (SEQ ID NO: 80)
*787 G2361A

| Ordering (EGT) | |
|---|---|
| CS1-EGFR T790M-For2-for | ACACTGACGACATGGTTCTAC ACCACCGTGCAGCTC (SEQ ID NO: 81) |
| C52-EGFR T790M-Rev2-rev | TACGGTAGCAGAGACTTGGTC TAGGGCATGAGCTGC (SEQ ID NO: 82) |
| CS1-EGFR T790M-For3-for | ACACTGACGACATGGTTCTAC AACCTCCACCGTGCA (SEQ ID NO: 83) |
| C52-EGFR T790M-Rev3-rev | TACGGTAGCAGAGACTTGGTC TCGAAGGGCATGAGCTGC (SEQ ID NO: 84) |
| CS1-EGFR T790M-For4-for | ACACTGACGACATGGTTCTAC ACCACCGTGCAACTC (SEQ ID NO: 85) |
| CS1-EGFR T790M-Rev4-rev | TACGGTAGCAGAGACTTGGTC TAGGGCATGAGCTGC (SEQ ID NO: 82) |
| EGFR T790 Blocker4 | C3-GCAGCTCATCACGC-C3 (SEQ ID NO: 15) |
| EGFR T790 Blocker2 | C3-GCAGCTCATCACGC-C3 (SEQ ID NO: 15) |
| EGFR T790 Blocker3 | C3-GCAGCTCATCACGC-C3 (SEQ ID NO: 15) |
| EGFR T790 Blocker4 | C3-GCTCATCACGCAGC-C3 (SEQ ID NO: 86) |

What is claimed is:

1. A method for enriching a target DNA sequence in a sample comprising cell-free DNA from a bodily fluid suspected of containing a low abundance target DNA sequence, wherein the target DNA sequence differs by one nucleotide from a reference DNA sequence present in the sample, and
the reference DNA sequence is more prevalent in the sample than the target DNA sequence, the method comprising (a) prepare a reaction mixture comprising the sample, a polymerase, two primers, and a blocker, wherein
the two primers, comprising a first primer hybridizing to the reference DNA sequence and a second primer hybridizing to the complement of the reference DNA sequence, each has a melting temperature ($T_m$) that is (i) above the $T_m$ of the blocker hybridized to the target DNA sequence, and (ii) below the $T_m$ of the blocker hybridized to the reference DNA sequence;
the blocker is fully complementary to the reference DNA sequence but not the target DNA sequence;
the two primers are fully complementary to the reference DNA sequence or its complement and the target DNA sequence or its complement;

(b) subjecting the reaction mixture to two or more cycles of
(1) heating the reaction mixture to a temperature above the $T_m$ of the blocker sequence hybridized to the reference DNA sequence; then
(2) cooling the reaction mixture to a temperature below the $T_m$ of the blocker sequence hybridized to the reference DNA sequence, allowing hybridization of the blocker, but not the primers, to the reference DNA sequence; then
(3) heating the reaction mixture to a temperature above the Tm of the blocker sequence hybridized to the reference DNA sequence; then
(4) cooling the reaction mixture to a temperature below the Tm of the primer sequences hybridized to the reference DNA sequence; then
(5) allowing extension of the primers by the polymerase, thereby enriching the target DNA sequence in the sample.

2. The method of claim 1, wherein the target DNA sequence is in EGFR Exon 20 and encodes a T790M mutation.

3. The method of claim 1, wherein at least one primer overlaps the blocker.

4. The method of claim 1, wherein the blocker consists of 40 base pairs or less.

5. The method of claim 1, wherein the 3' end of the blocker is blocked to prevent extension.

6. The method of claim 1, wherein the 5' end of the reference blocking sequence comprises a nucleotide that prevents 5' to 3' exonucleolysis by Taq DNA polymerase.

7. The method of claim 1, wherein at least one primer further comprises an adapter sequence that is not complementary to the reference sequence, target sequence, or complements thereof.

8. The method of claim 1, wherein the target sequence is a mutant sequence of BRAF, EGFR, c-MET, HER-2, HER-3, NRAS, PIK3CA, KRAS, AKT-1, MAP2PK, ER, AR, FGFR1, FGFR2, FGFR3, KIT, PDGFR1, PDFGR2, PDGFR3, TP53, or SMAD1.

9. The method of claim 1, wherein the target sequence is a mutant sequence of KRAS, EGFR, PIK3CA, TP53, or BRAF.

10. The method of claim 1, wherein after cycling, a sample of the reaction mixture is analyzed using one or more of the methods selected from the group consisting of: MALDI-TOF, HR-Melting, Di-deoxy-sequencing, Single-molecule sequencing, pyrosequencing, high-throughput sequencing, SSCP, RFLP, dHPLC, CCM, digital PCR and quantitative-PCR.

11. The method of claim 1, wherein an amplicon of less than 50 bp is amplified using the method.

12. The method of claim 1, wherein the bodily fluid is plasma, blood, serum or urine.

13. The method of claim 1, wherein the bodily fluid is urine.

14. The method of claim 1, wherein the extension of the primers by the polymerase is at the temperature below the Tm of the primer sequences hybridized to the reference DNA sequence.

15. A method for enriching a target DNA sequence in a sample comprising cell-free DNA from a bodily fluid suspected of containing a low abundance target DNA sequence, wherein the target DNA sequence differs by one nucleotide from a reference DNA sequence present in the sample, and
the reference DNA sequence is more prevalent in the sample than the target DNA sequence, the method comprising (a) prepare a reaction mixture comprising the sample, a polymerase, two primers, and a blocker, wherein the two primers, comprising a first primer hybridizing to the reference DNA sequence and a second primer hybridizing to the complement of the reference DNA sequence, each has a melting temperature ($T_m$) that is (i) above the $T_m$ of the blocker hybridized to the target DNA sequence, and (ii) below the $T_m$ of the blocker hybridized to the reference DNA sequence;

the blocker is fully complementary to the reference DNA sequence but not the target DNA sequence;

the two primers are fully complementary to the reference DNA sequence or its complement and the target DNA sequence or its complement;

(b) subjecting the reaction mixture to two or more cycles of (1) heating the reaction mixture to a temperature above the $T_m$ of the blocker sequence hybridized to the reference DNA sequence; then (2) cooling the reaction mixture to a temperature below the $T_m$ of the blocker sequence hybridized to the reference DNA sequence, allowing hybridization of the blocker, but not the primers, to the reference DNA sequence; then (3) heating the reaction mixture to a higher temperature below the $T_m$ of the blocker sequence hybridized to the reference DNA sequence; then (4) cooling the reaction mixture to a temperature below the Tm of the primer sequences hybridized to the reference DNA sequence; then (5) allowing extension of the primers by the polymerase, thereby enriching the target DNA sequence in the sample.

16. The method of claim 15, wherein the target DNA sequence is in KRAS Exon 2 and is a single base substitution from the reference sequence.

17. The method of claim 15, wherein the extension of the primers by the polymerase is at the temperature below the Tm of the primer sequences hybridized to the reference DNA sequence.

18. The method of claim 15, wherein at least one primer overlaps the blocker.

19. The method of claim 15, wherein an amplicon of less than 50 bp is amplified using the method.

20. The method of claim 15, wherein the bodily fluid is plasma, blood, serum or urine.

* * * * *